United States Patent
Sinha et al.

(10) Patent No.: US 8,530,462 B2
(45) Date of Patent: Sep. 10, 2013

(54) INDOLE MODULATORS OF S1P RECEPTORS

(75) Inventors: Santosh C. Sinha, Ladera Ranch, CA (US); Smita S. Bhat, Irvine, CA (US); Ken Chow, Newport Coast, CA (US); Michael E. Garst, Newport Beach, CA (US); Wha Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 13 days.

(21) Appl. No.: 13/293,821

(22) Filed: Nov. 10, 2011

(65) Prior Publication Data

US 2012/0129829 A1     May 24, 2012

Related U.S. Application Data

(60) Provisional application No. 61/416,958, filed on Nov. 24, 2010.

(51) Int. Cl.
| | |
|---|---|
| *A61K 31/4245* | (2006.01) |
| *A61K 31/4439* | (2006.01) |
| *A61K 31/4045* | (2006.01) |
| *C07D 413/04* | (2006.01) |
| *C07D 405/12* | (2006.01) |
| *C07D 209/42* | (2006.01) |
| *C07D 413/14* | (2006.01) |

(52) U.S. Cl.
USPC ...... 514/210.18; 514/364; 514/339; 514/415; 514/419; 546/269.4; 548/131; 548/364; 548/467; 548/492

(58) Field of Classification Search
USPC ........................ 514/364, 415; 548/131, 469
See application file for complete search history.

(56) References Cited

FOREIGN PATENT DOCUMENTS
| | | |
|---|---|---|
| WO | 2007095561 A2 | 8/2007 |
| WO | WO 2007095561 A2 * | 8/2007 |
| WO | WO 2008-076356 | 3/2009 |

OTHER PUBLICATIONS

Vippagunta et al., Advanced Drug Delivery Reviews, vol. 48, p. 3-26, (2001).*
Chapter 11 of Byrn et al., Solid-State Chemistry of Drugs (2nd Ed. 1999) (pp. 233-247).*
Hale, Jeffrey et al., "Potent S1P Receptor Agonists Replicate the Pharmacologic Actions of the Novel Immune Modulator FTY720", Bioorganic & Medicinal Chemistry Letters 14 (2004) 3351-3355.
Stahl, Heinrich et al., Handbook of Pharmaceutical Salts, Verlag Helvetica Chimica Acta—Zurich, 2002, 329-345.

* cited by examiner

*Primary Examiner* — Yong Chu
(74) *Attorney, Agent, or Firm* — Doina G. Ene

(57) ABSTRACT

The present invention relates to novel indole derivatives, processes for preparing them, pharmaceutical compositions containing them and their use as pharmaceuticals as modulators of sphingosine-1-phosphate receptors.

14 Claims, No Drawings

INDOLE MODULATORS OF S1P RECEPTORS

CROSS REFERENCE TO RELATED APPLICATIONS

This application claims the benefit of U.S. Provisional Application Ser. No. 61/416,958 filed Nov. 24, 2010, which is hereby incorporated by reference in its entirety.

FIELD OF THE INVENTION

The present invention relates to novel indole derivatives, processes for preparing them, pharmaceutical compositions containing them and their use as pharmaceuticals, as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

A group of novel indole derivatives which are potent and selective sphingosine-1-phosphate modulators, has been discovered. As such, the compounds described herein are useful in treating a wide variety of disorders associated with modulation of sphingosine-1-phosphate receptors. The term-"modulator" as used herein, includes but is not limited to: receptor agonist, antagonist, inverse agonist, inverse antagonist, partial agonist, partial antagonist.

In one embodiment, this document describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect the invention provides a compound having Formula I or a pharmaceutically acceptable salt thereof or steroisomeric forms thereof, and the geometrical isomers, enantiomers, diasteroisomers, tautomers, zwitterions and pharmaceutically acceptable salts thereof:

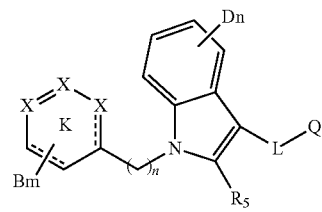

Formula I wherein:
K is aryl or heteroaryl containing 1 to 2 N, O or S atoms, unsubstituted or substituted by 1, 2 or 3 substituents selected but not limited to: halogen, alkoxy, alkyl, amino, ester, carboxylic acid, amides, ether, hydroxyl or cycloalkyl moieties;

X is the same or is independently C or N;

B is the same or is independently $C_{1-4}$ alkyl, cyclic or branched chain alkyl having 3 to 10 carbons, methoxy, hydrogen, hydroxyl, halogen, nitrile, trifluoromethyl, carboxy group, alkoxy, amino, ester, carboxylic acid, amides, ether, cycloalkyl moieties, $C_{(1-6)}$ alkenyl straight or branched chain hydrocarbon, $C_{(3-6)}$ saturated or unsaturated cyclic hydrocarbon, aryl, heteroaryl, haloalkyl, hydroxyalkyl, alkylcarbonyl, formyl, oxycarbonyl, carboxyl, alkyl carboxylate, alkylamide, alkylamino or aminocarbonyl;

D is the same or is independently $C_{1-4}$ alkyl, cyclic or branched chain alkyl having 3 to 10 carbons, methoxy, hydrogen, hydroxyl, halogen, nitrile, trifluoromethyl, carboxy group, alkoxy, amino, ester, carboxylic acid, amides, ether, cycloalkyl moieties, $C_{(1-6)}$ alkenyl straight or branched chain hydrocarbon, $C_{(3-6)}$ saturated or unsaturated cyclic hydrocarbon, aryl, heteroaryl, haloalkyl, hydroxyalkyl, alkylcarbonyl, formyl, oxycarbonyl, carboxyl, alkyl carboxylate, alkylamide, alkylamino or aminocarbonyl;

M is 1, 2, 3, 4 or 5;
n is 1, 2, 3, 4 or 5;
L is one of the following structures:

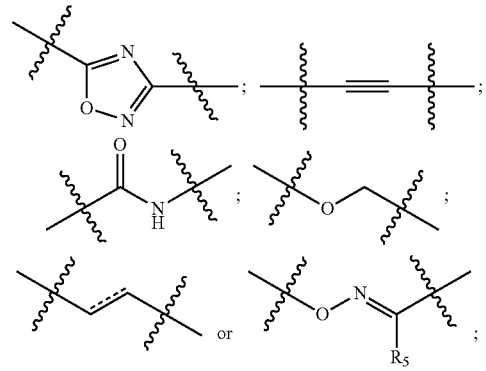

Q is one of the following structures:

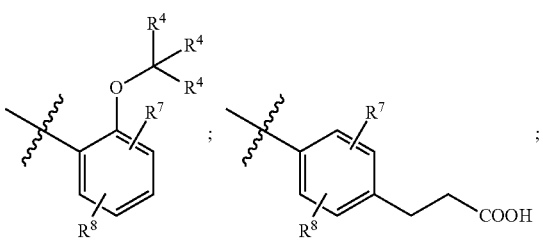

-continued

[Structures shown: aryl group with R⁷, R⁸ substituents and SO₂NH₂; aryl with R⁷, R⁸; aryl with R⁷, R⁸ and COOH; aryl with R⁷, R⁸ and NR⁵(CH₂)ₚCO₂R⁶; aryl with R⁷, R⁸ and azetidine-CO₂R⁶; pyridine with NHR³ and R⁷; aryl with R⁷, R⁸ and imidazole]

R³ is C₁₋₃ alkyl;
R⁴ is H or F;
R⁵ is H or Methyl;
R⁶ is H or Methyl;
p is 1, 2, 3 or 4;
R⁷ is H, C₁₋₁₀ alkyl, cyclic or branched chain alkyl having 3 to 10 carbons, alkoxy, hydroxyl, aminoalkyl, halogen, nitrile, trifluoromethyl, carboxy group, substituted or unsubstituted aryl, heteroaryl or heterocyclic;
R⁸ is H, C₁₋₁₀ alkyl, cyclic or branched chain alkyl having 3 to 10 carbons, alkoxy, hydroxyl, aminoalkyl, halogen, nitrile, trifluoromethyl, carboxy group, substituted or unsubstituted aryl, heteroaryl or heterocyclic.

In another aspect the invention provides a compound having Formula I wherein:
K is aryl, unsubstituted or substituted by 1, 2 or 3 substituents selected but not limited to: halogen, alkoxy, alkyl, amino, carboxylic acid or hydroxyl;
X is C;
B is the same or is independently C₁₋₄ alkyl, methoxy, hydrogen, hydroxyl, halogen, nitrile, trifluoromethyl, amino, carboxylic acid or alkoxy;
D is C₁₋₄ alkyl, methoxy, hydrogen, hydroxyl, halogen, nitrile, trifluoromethyl, amino or carboxylic acid;
m is 1 or 2;
n is 1;
L is

[Structures: 1,2,4-oxadiazole or amide (C(=O)NH)]

Q is one of the following structures:

[Structures: aryl with R⁷, R⁸ and NR⁵(CH₂)ₚCO₂R⁶; aryl with R⁷, R⁸ and azetidine-CO₂R⁶; pyridine with NHR³ and R⁷; aryl with R⁷, R⁸ and imidazole]

R³ is C₁₋₃ alkyl;
R⁵ is H or Methyl;
R⁶ is H or Methyl;
p is 1, 2, 3 or 4;
R⁷ is H, alkyl 1 to 10 carbons, aminoalkyl, halogen, nitrile or trifluoromethyl;
R⁸ is H, alkyl 1 to 10 carbons, aminoalkyl, halogen, nitrile or trifluoromethyl.

In another aspect the invention provides a compound having Formula I wherein:
K is aryl, unsubstituted or substituted by 1, 2 or 3 substituents selected but not limited to: halogen, alkoxy, alkyl, amino, carboxylic acid or hydroxyl;
X is C;
B is the same or is independently C₁₋₄ alkyl, methoxy, hydrogen, hydroxyl, halogen, nitrile, trifluoromethyl, amino, carboxylic acid or alkoxy;
D is C₁₋₄ alkyl, methoxy, hydrogen, hydroxyl, halogen, nitrile, trifluoromethyl, amino or carboxylic acid;
m is 1 or 2;
n is 1;
L is

[Structure: amide C(=O)NH]

Q is one of the following structures:

[Structures: aryl with R⁷, R⁸ and NR⁵(CH₂)ₚCO₂R⁶ or aryl with R⁷, R⁸ and azetidine-CO₂R⁶]

R⁵ is H or Methyl;
R⁶ is H or Methyl;

p is 1, 2, 3 or 4;

$R^7$ is H, $C_{1-10}$ alkyl, aminoalkyl, halogen, nitrile or trifluoromethyl;

$R^8$ is H, $C_{1-10}$ alkyl, aminoalkyl, halogen, nitrile or trifluoromethyl.

In another aspect the invention provides a compound having Formula I wherein:

K is aryl, unsubstituted or substituted by 1, 2 or 3 substituents selected but not limited to: halogen, alkoxy, alkyl, amino, carboxylic acid or hydroxyl;

X is C;

B is the same or is independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino or carboxylic acid;

m is 1 or 2;

n is 1;

L is

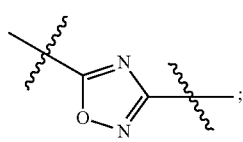 [SMILES: *c1noc(*)n1]

Q is one of the following structures:

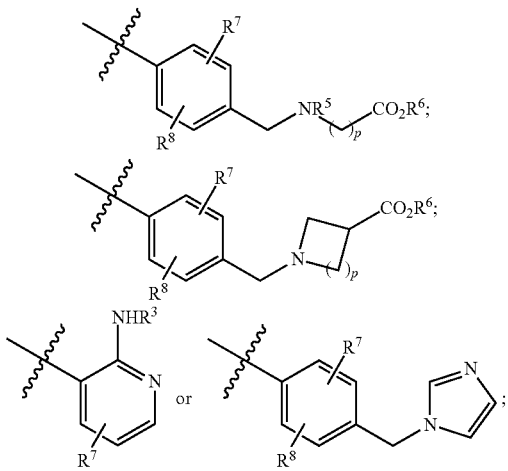

$R^3$ is $C_{1-3}$ alkyl;

$R^5$ is H or Methyl;

$R^6$ is H or Methyl;

p is 1, 2, 3 or 4;

$R^7$ is H, $C_{1-10}$ alkyl, aminoalkyl, halogen, nitrile or trifluoromethyl;

$R^8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

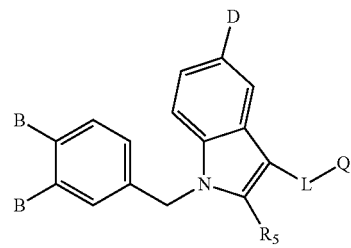

Formula II wherein:

B is the same or is independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino or carboxylic acid:

L is

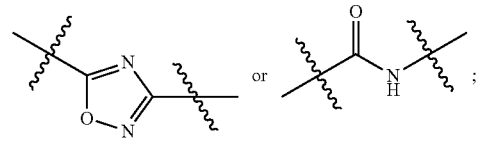 [SMILES: *c1noc(*)n1 ; *NC(*)=O]

Q is one of the following structures:

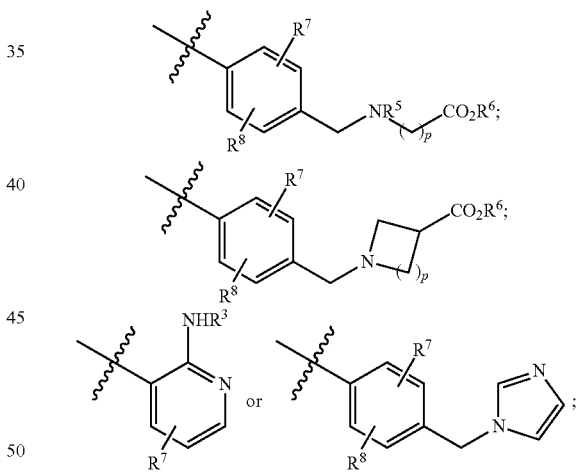

$R^3$ is $C_{1-3}$ alkyl;

$R^5$ is H or Methyl;

$R^6$ is H or Methyl;

p is 1, 2, 3 or 4;

$R^7$ is H, $C_{1-10}$ alkyl, aminoalkyl, halogen, nitrile or trifluoromethyl;

$R^8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

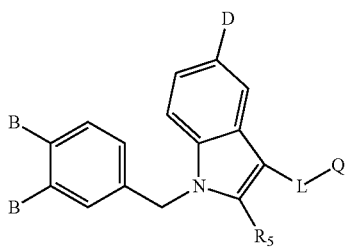

Formula II wherein:

B is the same or is independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino or carboxylic acid;

L is

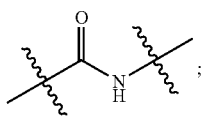 [SMILES: *NC(*)=O]

Q is one of the following structures:

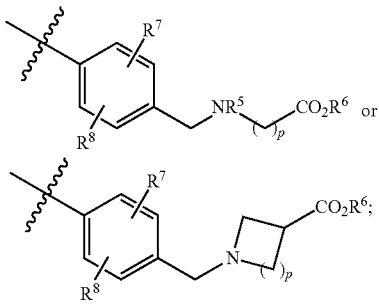

$R^5$ is H or Methyl;
$R^6$ is H or Methyl;
p is 1, 2, 3 or 4;
$R^7$ is H, $C_{1-10}$ alkyl, aminoalkyl, halogen, nitrile or trifluoromethyl;
$R^8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

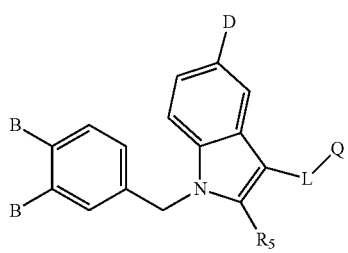

Formula II wherein:

B is the same or is independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino or carboxylic acid;

L is

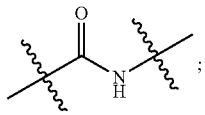 [SMILES: *NC(*)=O]

Q is

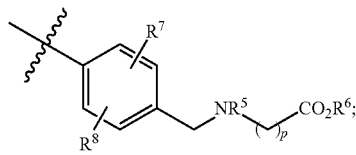

$R^5$ is H or Methyl;
$R^6$ is H or Methyl;
p is 1, 2, 3 or 4;
$R^7$ is H, $C_{1-10}$ alkyl, aminoalkyl, halogen, nitrile or trifluoromethyl;
$R^8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

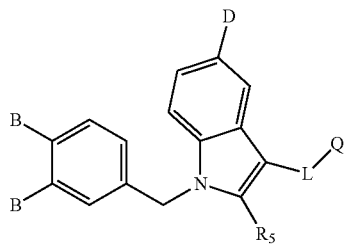

Formula II wherein:

B is the same or independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino, carboxylic acid;

L is

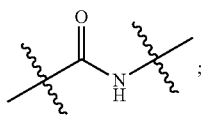 [SMILES: *NC(*)=O]

Q is

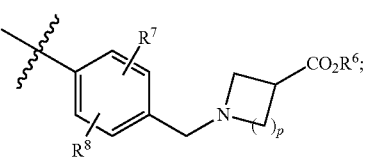

$R^5$ is H or Methyl;
$R^6$ is H or Methyl;
p is 1, 2, 3 or 4;
$R_7$ is H, $C_{1-10}$ alkyl, aminoalkyl, halogen, nitrile or trifluoromethyl;

$R_8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

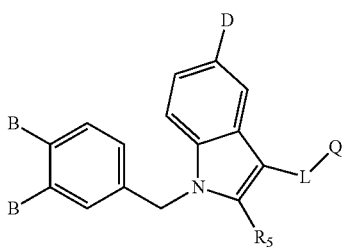

Formula II wherein:

B is the same or is independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino, carboxylic acid;

L is

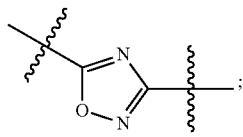 [SMILES: *c1noc(*)n1]

Q is one of the following structures:

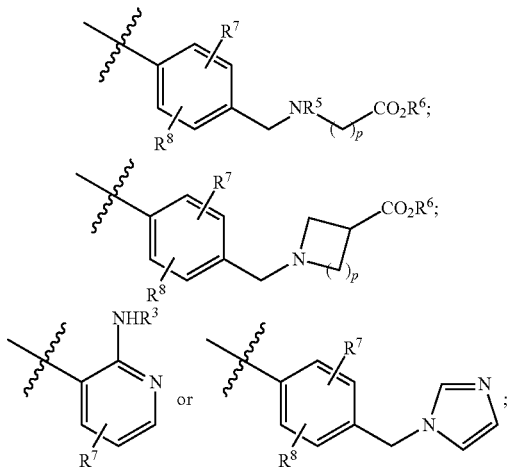

$R^3$ is $C_{1-3}$ alkyl;
$R^5$ is H or Methyl;
$R^6$ is H or Methyl;
p is 1, 2, 3 or 4;
$R^7$ is H, $C_{1-10}$ alkyl, aminoalkyl, halogen, nitrile or trifluoromethyl;
$R^8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

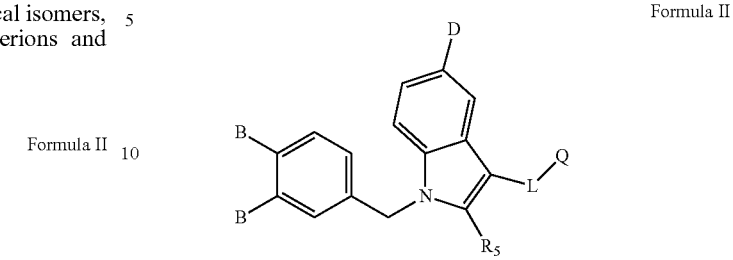

Formula II wherein:

B is the same or is independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino, carboxylic acid;

L is

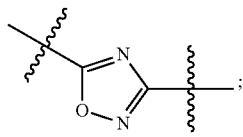 [SMILES: *c1noc(*)n1]

Q is

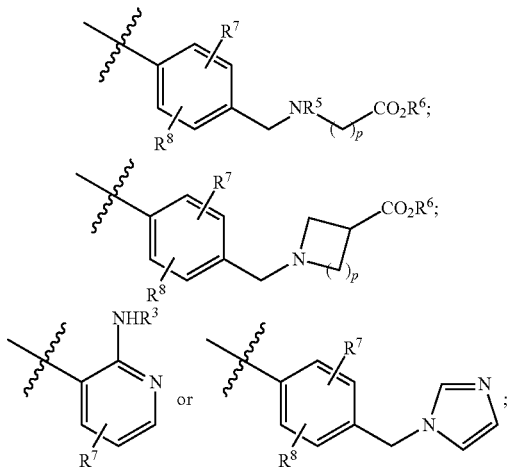

$R^5$ is H or Methyl;
p is 1, 2, 3 or 4;
$R^7$ is H, $C_{1-10}$ alkyl, aminoalkyl, halogen, nitrile or trifluoromethyl;
$R^8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

Formula II wherein:

B is the same or is independently $C_{1-4}$ alkyl, methoxy, hydrogen, hydroxyl, halogen, nitrile, trifluoromethyl, amino, carboxylic acid or alkoxy;

D is $C_{1-4}$ alkyl, methoxy, hydrogen, hydroxyl, halogen, nitrile, trifluoromethyl, amino, carboxylic acid;

L is

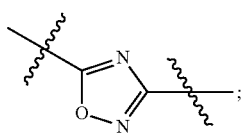 [SMILES: *c1noc(*)n1]

Q is

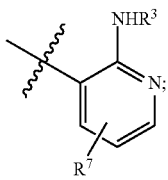

$R^3$ is $C_{1-3}$ alkyl;
$R^5$ is H or Methyl;
p is 1, 2, 3 or 4;
$R^7$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

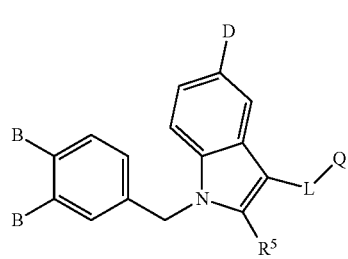

Formula II wherein:
B is the same or is independently $C_{1-4}$ alkyl, methoxy, hydrogen, hydroxyl, halogen, nitrile, trifluoromethyl, amino, carboxylic acid or alkoxy;
D is $C_{1-4}$ alkyl, methoxy, hydrogen, hydroxyl, halogen, nitrile, trifluoromethyl, amino, carboxylic acid;
L is

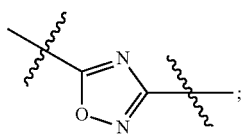 [SMILES: *c1noc(*)n1]

Q is

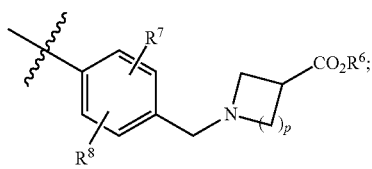

$R^5$ is H or Methyl;
$R^6$ is H or Methyl;
p is 1, 2, 3 or 4;
$R^7$ is H, $C_{1-10}$ alkyl, aminoalkyl, halogen, nitrile or trifluoromethyl;
$R^8$ is H, $C_{1-10}$ alkyl, aminoalkyl, halogen, nitrile or trifluoromethyl.

In another aspect the invention provides a compound having Formula II or a pharmaceutically acceptable salt thereof or steroisomeric forms thereof, and the geometrical isomers, enantiomers, diasteroisomers, tautomers, zwitterions and pharmaceutically acceptable salts thereof:

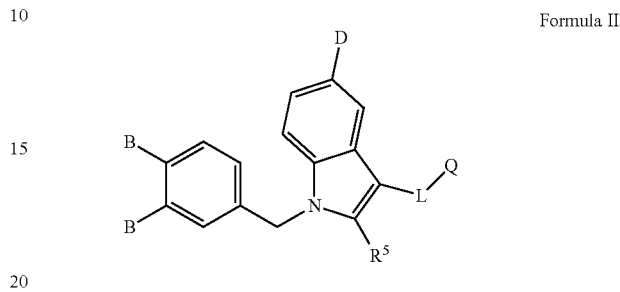

Formula II wherein:
B is the same or is independently $C_{1-4}$ alkyl, methoxy, hydrogen, hydroxyl, halogen, nitrile, trifluoromethyl, amino, carboxylic acid or alkoxy;
D is $C_{1-4}$ alkyl, methoxy, hydrogen, hydroxyl, halogen, nitrile, trifluoromethyl, amino, carboxylic acid;
L is

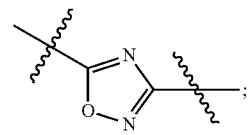 [SMILES: *c1noc(*)n1]

Q is

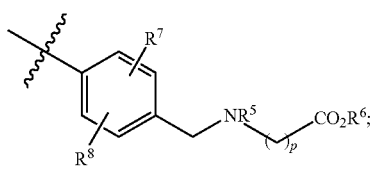

$R^5$ is H or Methyl;
$R^6$ is H or Methyl;
p is 1, 2, 3 or 4;
$R^7$ is H, $C_{1-10}$ alkyl, aminoalkyl, halogen, nitrile or trifluoromethyl;
$R^8$ is H, $C_{1-10}$ alkyl, aminoalkyl, halogen, nitrile or trifluoromethyl.

The term "alkyl", as used herein, refers to saturated, monovalent hydrocarbon moieties having linear or branched moieties or combinations thereof and containing 1-10 carbon atoms. One methylene (—$CH_2$—) group, of the alkyl can be replaced by oxygen, sulfur, sulfoxide, nitrogen, carbonyl, carboxyl, sulfonyl, phosphate or by a divalent ($C_{3-6}$ cycloalkyl). Alkyl moieties can optionally be substituted by halogen atoms, hydroxyl groups, cycloalkyl groups, amino groups, heterocycles groups, carboxylic acid groups, phosphonic acid groups, sulphonic acid groups, phosphoric acid groups.

The term "cycloalkyl", as used herein, refers to a monovalent or divalent group of 3 to 8 carbon atoms, derived from a saturated cyclic hydrocarbon. Cycloalkyl can be optionally substituted by $C_{1-3}$ alkyl groups or halogen atoms.

The term "halogen", as used herein, refers to an atom of chlorine, bromine, fluorine, iodine.

The term "heterocycle" as used herein, refers to a 3 to 10 membered ring, containing at least one heteroatom selected form O or N or S or combinations of at least two thereof interrupting the carbocyclic ring structure. The heterocyclic ring can be monocyclic or polycyclic. The heterocyclic ring can be saturated or non-saturated. The heterocyclic ring can be interrupted by a C=O, the S heteroatom can be oxidized. Heterocyclic ring moieties can optionally be substituted by hydroxyl, $C_{1-3}$ alkyl groups or halogen atoms.

The term "aryl" as used herein, is defined as including an organic moiety derived from an aromatic hydrocarbon consisting of a ring containing 6 to 10 carbon atoms by removal of one hydrogen. Aryl can optionally be substituted by halogen atoms halogen atoms, hydroxyl groups, cycloalkyl groups, amino groups, heterocycles groups, carboxylic acid groups, phosphonic acid groups, sulphonic acid groups, phosphoric acid groups. Aryl can be monocyclic or polycyclic.

The term "methoxy" as used herein, represents a group of formula "—$OCH_3$".

The term "trifluoromethyl" as used herein, represents a group of formula "—$CF_3$".

The term "amino" as used herein, represents a group of formula "—$NH_2$".

The term "alkoxy" as used herein, represents a group of formula "—$OC_{1-10}$ alkyl".

The term "hydroxyl" as used herein, represents a group of formula "—OH".

The term "carbonyl" as used herein, represents a group of formula "—C=O".

The term "carboxyl" as used herein, represents a group of formula "—C(O)O—".

The term "cyano" or "nitrile" as used herein, represents a group of formula "—CN".

The term "aldehyde" as used herein, represents a group of formula "—C(O)H".

The term "sulfate" as used herein, represents a group of formula "—$SO_2$".

The term "sulfonyl" as used herein, represents a group of formula "—O—$S(O)_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—$P(O)(OH)_2$".

The term "phosphoric acid" as used herein, represents a group of formula "—$(O)P(O)(OH)_2$".

The term "sulphonic acid" as used herein, represents a group of formula "—$S(O)_2OH$".

The term "aminoalkyl" as used herein, represents a group of formula "—$NH(C_{1-6}$ alkyl) or "—$N(C_{1-6}$ alkyl)($C_{1-6}$ alkyl)".

Some compounds of the invention are:
3-[(4-{5-[1-(3,4-dimethylbenzyl)-5-methyl-1H-indol-3-yl]-1,2,4-oxadiazol-3-yl}benzyl)amino]propanoic acid;
1-{4-[5-(1-benzyl-5-fluoro-1H-indol-3-yl)-1,2,4-oxadiazol-3-yl]benzyl}azetidine-3-carboxylic acid;
1-(4-{5-[1-(3,4-dimethylbenzyl)-5-methoxy-2-methyl-1H-indol-3-yl]-1,2,4-oxadiazol-3-yl}benzyl)azetidine-3-carboxylic acid;
3-[(4-{5-[1-(3,4-dimethylbenzyl)-5-fluoro-1H-indol-3-yl]-1,2,4-oxadiazol-3-yl}benzyl)amino]propanoic acid;
1-benzyl-3-{3-[4-(1H-imidazol-1-ylmethyl)phenyl]-1,2,4-oxadiazol-5-yl}-1H-indole;
3-({4-[5-(1-benzyl-5-fluoro-1H-indol-3-yl)-1,2,4-oxadiazol-3-yl]benzyl}amino)propanoic acid;
1-{4-[5-(1-benzyl-1H-indol-3-yl)-1,2,4-oxadiazol-3-yl]benzyl}azetidine-3-carboxylic acid;
3-[5-(1-benzyl-1H-indol-3-yl)-1,2,4-oxadiazol-3-yl]-N-methylpyridin-2-amine;
1-(3,4-dimethylbenzyl)-5-fluoro-3-{3-[4-(1H-imidazol-1-ylmethyl)phenyl]-1,2,4-oxadiazol-5-yl}-1H-indole;
1-(4-{5-[1-(3,4-dimethylbenzyl)-5-fluoro-1H-indol-3-yl]-1,2,4-oxadiazol-3-yl}benzyl)azetidine-3-carboxylic acid;
1-(4-{5-[1-(3,4-dimethylbenzyl)-5-fluoro-2-methyl-1H-indol-3-yl]-1,2,4-oxadiazol-3-yl}benzyl)azetidine-3-carboxylic acid;
3-({4-[5-(1-benzyl-1H-indol-3-yl)-1,2,4-oxadiazol-3-yl]benzyl}amino)propanoic acid;
3-{5-[1-(3,4-dimethylbenzyl)-5-fluoro-1H-indol-3-yl]-1,2,4-oxadiazol-3-yl}-N-methylpyridin-2-amine;
1-(4-{5-[1-(3,4-dimethylbenzyl)-1H-indol-3-yl]-1,2,4-oxadiazol-3-yl}benzyl)azetidine-3-carboxylic acid;
3-[(4-{5-[1-(3,4-dimethylbenzyl)-1H-indol-3-yl]-1,2,4-oxadiazol-3-yl}benzyl)amino]propanoic acid;
1-(4-{5-[1-(3,4-dimethylbenzyl)-5-methyl-1H-indol-3-yl]-1,2,4-oxadiazol-3-yl}benzyl)azetidine-3-carboxylic acid;
5-({4-[5-(1-benzyl-1H-indol-3-yl)-1,2,4-oxadiazol-3-yl]benzyl}amino)pentanoic acid.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I or Formula II are able to form.

The acid addition salt form of a compound of Formula I or Formula II that occurs in its free form as a base can be obtained by treating the free base with an appropriate acid such as an inorganic, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zurich, 2002, 329-345).

Compounds of Formula I or of Formula II and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above Formulae, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation.

Therapeutic utilities of S1P modulators are:

Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or of Formula II or a pharmaceutically acceptable salt thereof, for the manufacture of a medicament for the treatment of:

Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula II.

The compounds of Formula II according to the invention can be prepared analogously to conventional methods as understood by the person skilled in the art of synthetic organic chemistry.

The following abbreviations are used in the general schemes and in the examples:

DCM or $CH_2Cl_2$ dichloromethane $CDCl_3$ deuterated chloroform

MeOH methanol $CD_3OD$ deuterated methanol

DMF N,N dimethylformamide

EDCI 1-ethyl-3-(3-dimethylaminopropyl)carbodiimide

HOBt Hydroxybenzotriazole

THF tertahydrofuran $CH_3CN$ acetonitrile

EtOAc ethylacetate

HCl hydrochloric acid $MgSO_4$ magnesium sulfate

MPLC medium pressure column chromatography $NaHCO_3$ sodium bicarbonate

CDI 1,1'-Carbonyldiimidazole

TPAP tetrapropylammonium perruthenate

NMO N-methylmorpholine-N-oxide

AcOH acetic acid $NaCNBH_3$ Sodium cyanoborohydride

General Scheme for Obtaining Compounds of Formula II Wherein
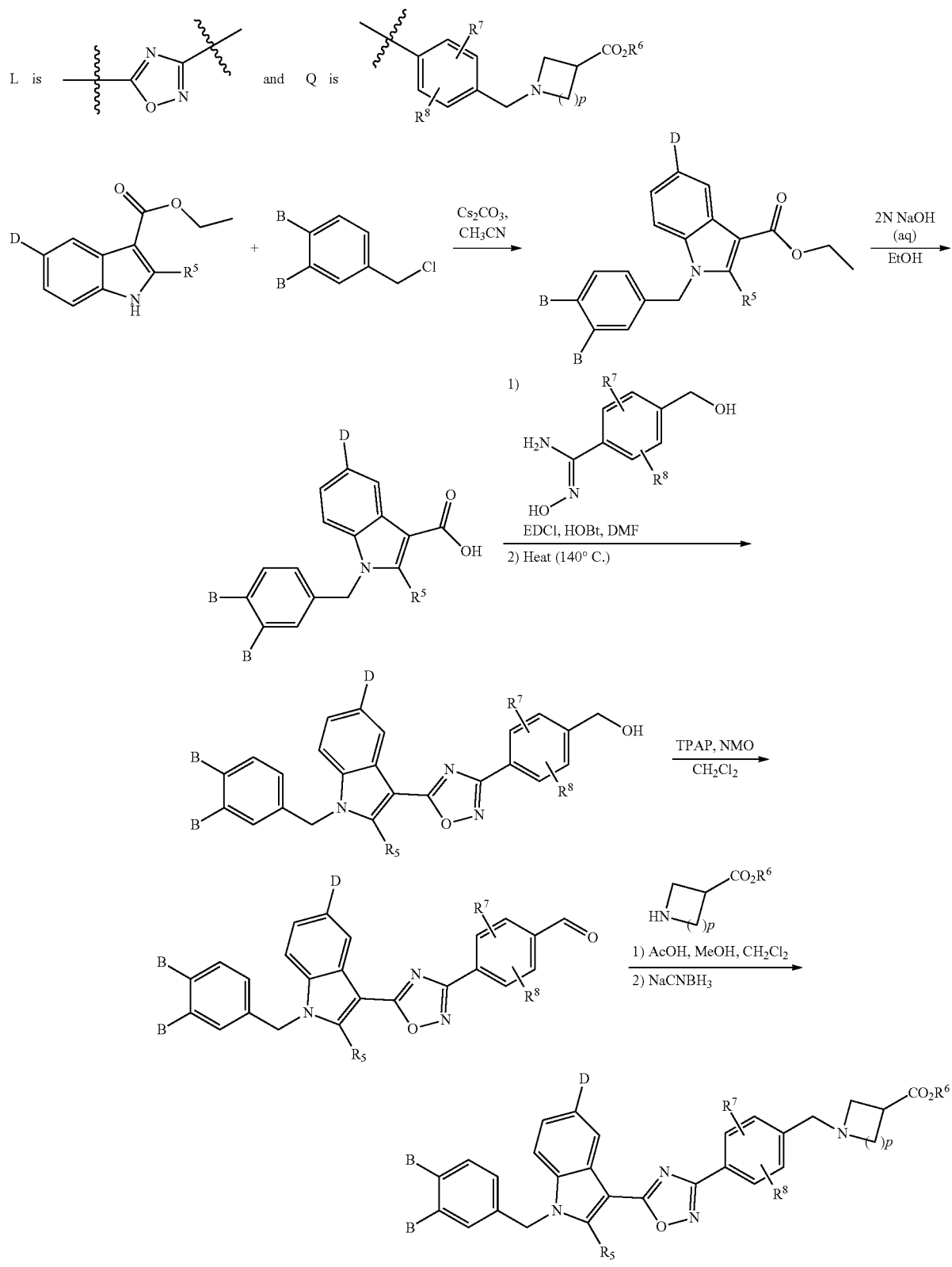
Formula II General Scheme for Obtaining Compounds of Formula II Wherein
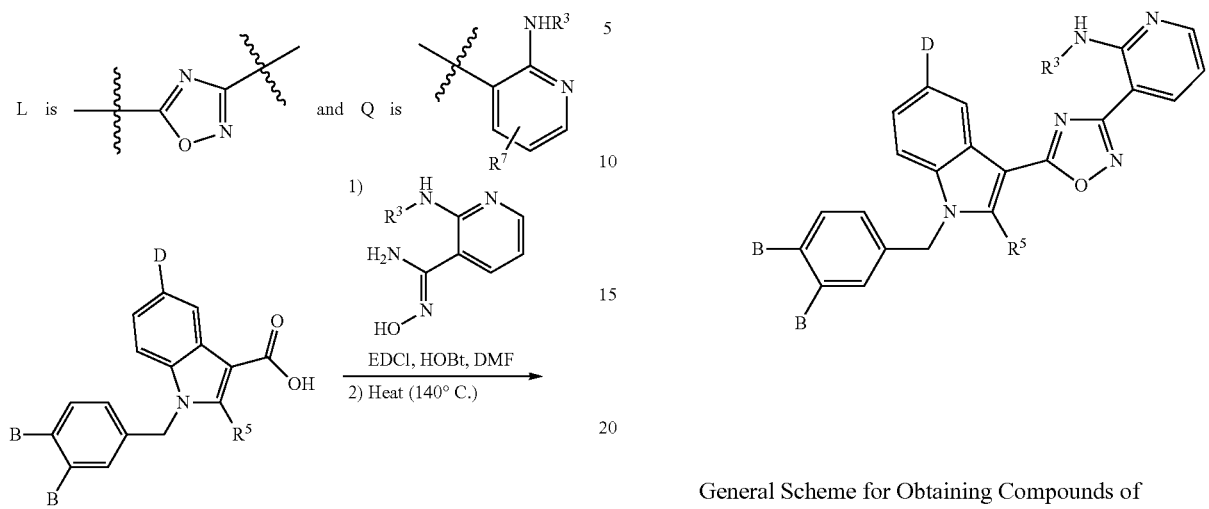
General Scheme for Obtaining Compounds of Formula II Wherein
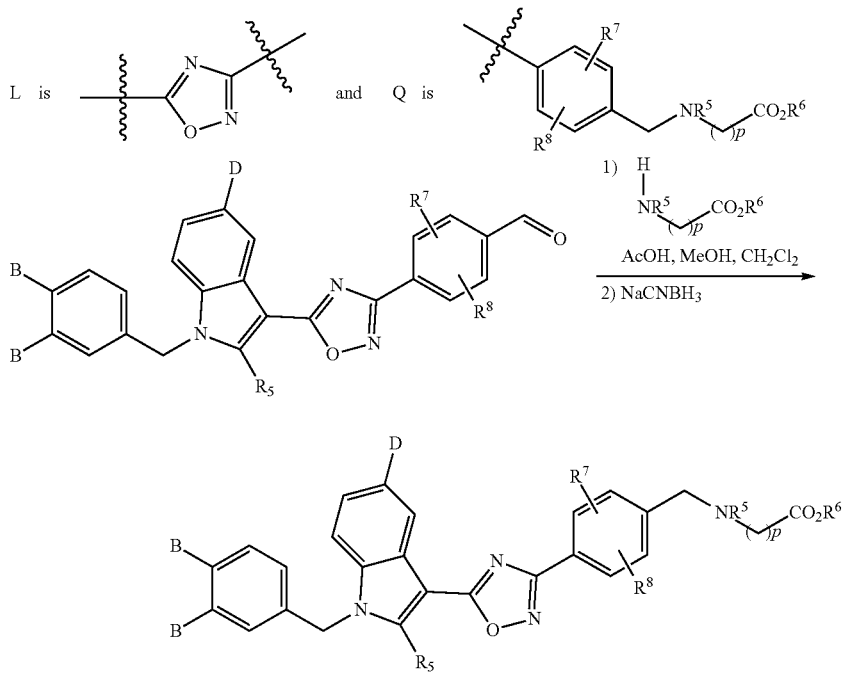
General Scheme for Obtaining Compounds of Formula II Wherein
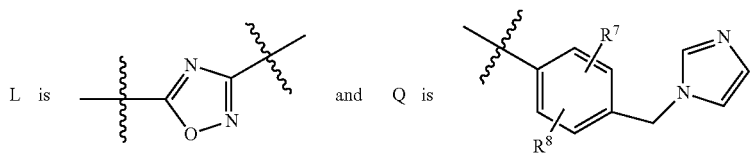

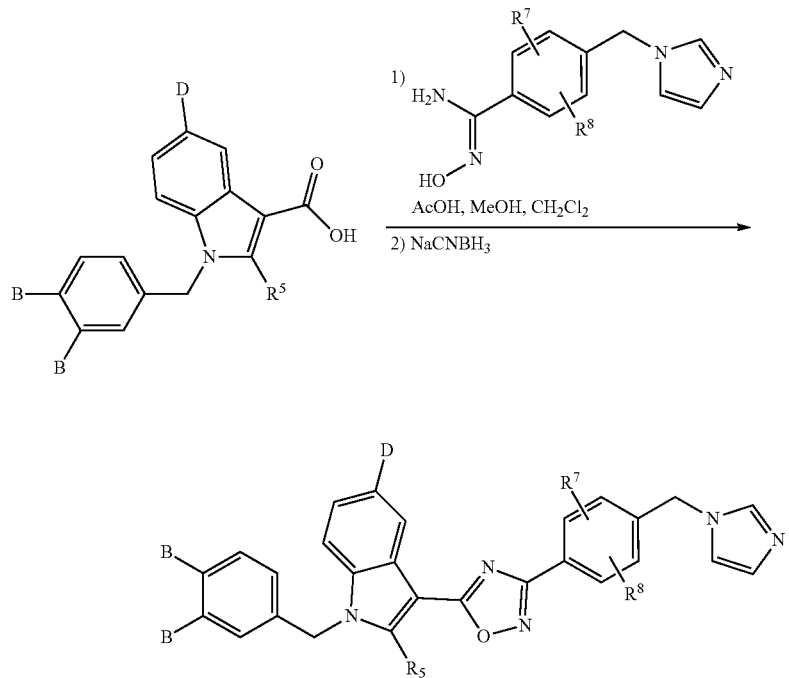
General Scheme for Obtaining Compounds of Formula II Wherein
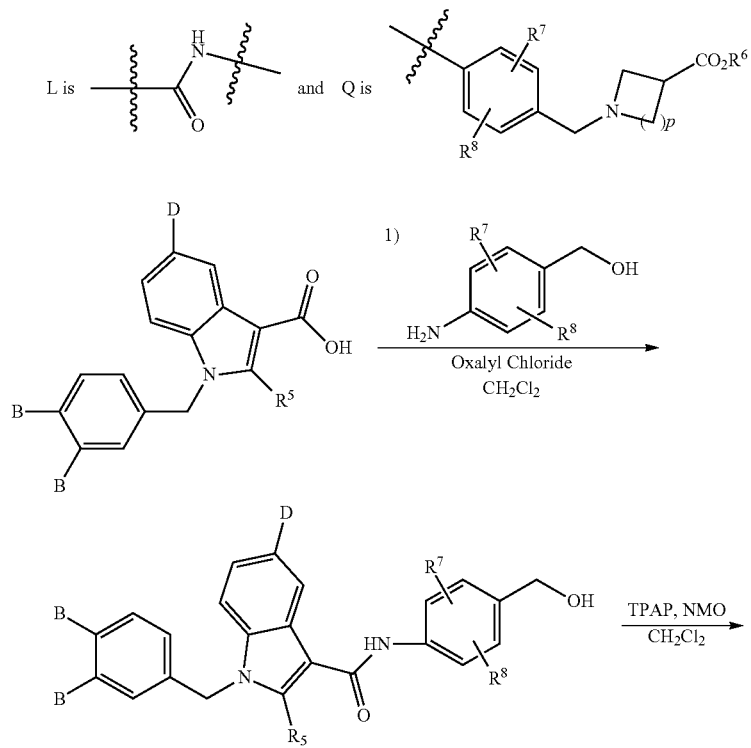

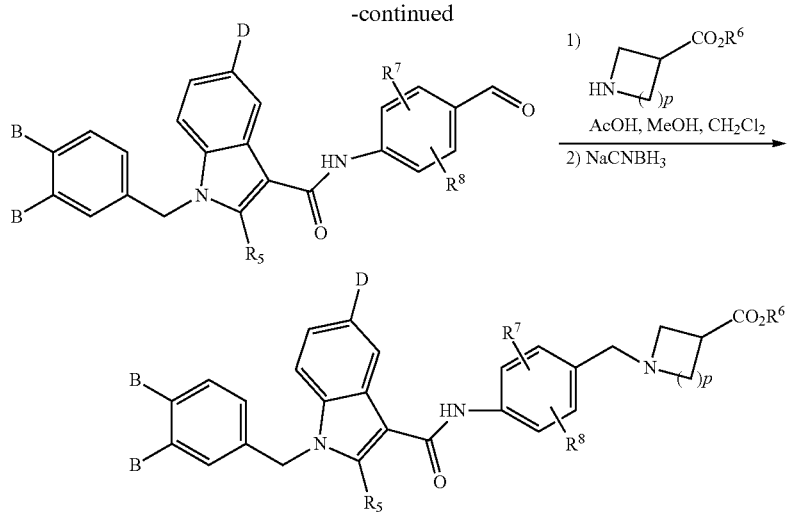

General Scheme for Obtaining Compounds of Formula II Wherein

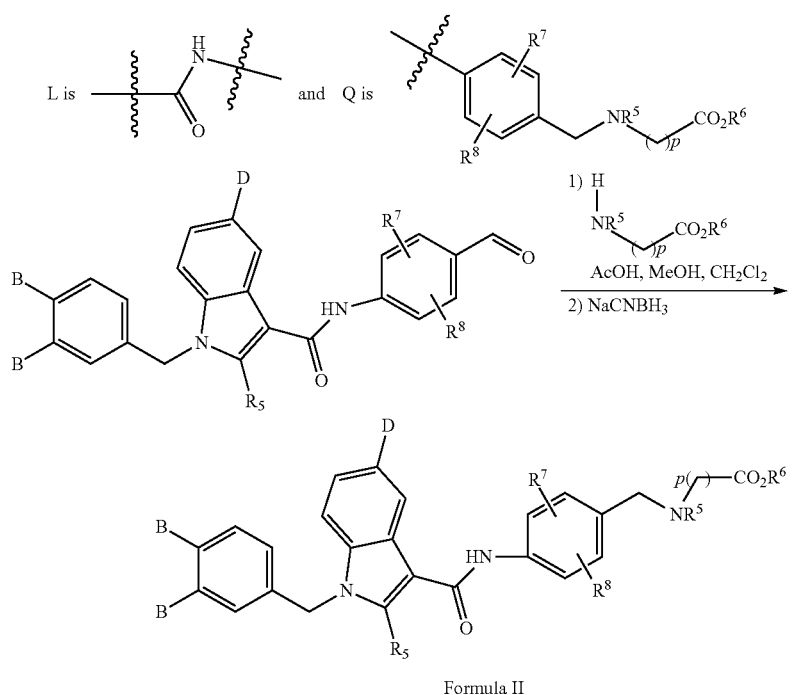

Formula II

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

The IUPAC names of the compounds mentioned in the examples were generated with ACD version 8 and intermediates and reagent names used in the examples were generated with software such as Chem Bio Draw Ultra version 12.0 or Auto Nom 2000 from MDL ISIS Draw 2.5 SP1.

Unless specified otherwise in the examples, characterization of the compounds is performed with NMR spectra which are recorded on 300 or 600 MHz Varian and acquired at room temperature. Chemical shifts are given in ppm referenced either to internal trimethylsilyl or to the residual solvent signal.

All the reagents, solvents, catalysts for which the synthesis is not described are purchased from chemical vendors such as Sigma Aldrich, Fluka, Bio-Blocks, Ryan Scientific, Syn Chem, Chem-Impex, Aces Pharma, however some known intermediates, for which the CAS registry number [CAS #] are mentioned, were prepared in-house following known procedures.

Usually the compounds of the invention were purified by flash column chromatography using a gradient solvent system of methanol/dichloromethane unless otherwise reported. The following synthetic schemes illustrate how compounds according to the invention can be made. Those skilled in the art will be routinely able to modify and/or adapt the following schemes to synthesize any compound of the invention covered by Formula II.

Example 1

Intermediate 1

1-(3,4-dimethylbenzyl)-5-methyl-1H-indole-3-carboxylate

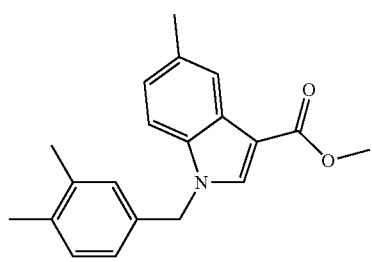

To a solution of 5-methyl-1H-indole-3-methyl carboxylate, (CAS 227960-12-5) (3 g, 10.58 mmol) in CH$_3$CN (60 mL) was added cesium carbonate (10.3 g, 31.7 mmol) and the suspension was stirred at reflux temperature for 2 hrs. The mixture was then cooled at 50° C. and 4-(chloromethyl)-1,2-dimethylbenzene, (2.7 g, 17.5 mmol) was added slowly. The reaction mixture was stirred at reflux temperature for 1 hr. The reaction was cooled to room temperature and filtered to remove cesium carbonate, concentrated and gave Intermediate 1 (4.8 g).

$^1$H NMR (300 MHz, CDCl$_3$) δ: 7.98 (s, 1H), 7.78 (s, 1H), 7.18-7.28 (m, 1H), 7.01-7.13 (m, 2H), 6.84-6.97 (m, 2H), 5.22 (s, 2H), 3.90 (s, 3H), 2.47 (s, 3H), 2.21 (d, 6H).

Example 2

Intermediate 2

1-(3,4-dimethylbenzyl)-5-methyl-1H-indole-3-carboxylic acid

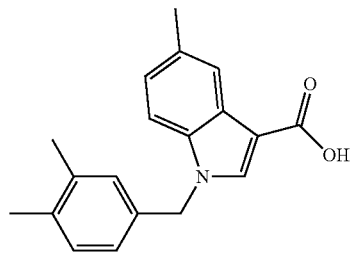 [SMILES: Cc1ccc2c(c1)c(C(=O)O)cn2Cc1ccc(C)c(C)c1]

Sodium hydroxide solution (3N, 15 mL) was added to a solution of Intermediate 1 (3 g, 9.77 mmol) in 45 mL of THF/MeOH (1.5:0.5) at room temperature. After stirring at 80° C. for 16 h, the mixture was cooled to room temperature and the solvents were evaporated. The residue was diluted with ethyl acetate (50 mL) and acidified with 3N HCl (aq.) at 0° C. The mixture was then extracted with EtOAc (3×100 mL), washed with brine (1×100 mL), dried (MgSO$_4$) filtered and concentrated to give a crude colorless solid. Purification by MPLC using EtOAc and hexane afforded Intermediate 2 (2.6 g, 90% yield) as a white solid.

$^1$H NMR (300 MHz, CDCl$_3$) δ: 8.04 (s, 1H), 7.86 (s, 1H), 7.23 (d, J=8.5 Hz, 1H), 7.08 (d, J=7.6 Hz, 2H), 6.84-7.00 (m, 2H), 5.24 (s, 2H), 2.48 (s, 3H), 2.22 (d, 6H).

Example 3

Intermediate 3

(4-(5-(1-(3,4-dimethylbenzyl)-5-methyl-1H-indol-3-yl)-1,2,4-oxadiazol-3-yl)phenyl)methanol

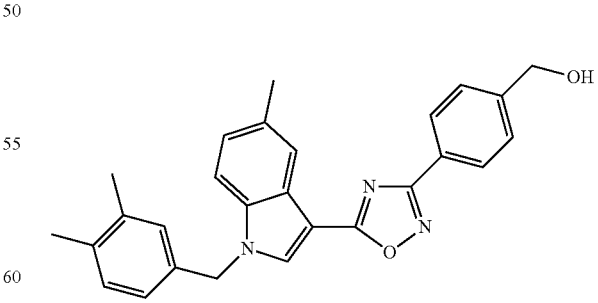

To a solution of Intermediate 2 (1.1 g, 3.7 mmol) in DMF (15 mL) was added EDCI (768 mg, 4 mmol) at room temperature. The mixture was stirred at room temperature for 30 minutes then (Z)—N'-hydroxy-4-(hydroxymethyl)benzimidamide, (CAS 1233243-49-6) (676 mg, 4 mmol) was added to the reaction mixture at room temperature. The mixture was stirred at room temperature for 30 minutes then at 80° C. for 2 hrs. The reaction was then cooled to room temperature, most of the DMF was removed under reduced pressure and the residue was diluted with EtOAc and quenched with 0.5 N HCl. The mixture was then extracted with EtOAc (3×50 mL), washed with NaHCO₃ (aq.), brine (1×100 mL), dried (MgSO₄) filtered and concentrated to give a crude product. Purification by MPLC using EtOAc and hexane afforded Intermediate 3 (726 mg, 47% yield).

$^1$H NMR (300 MHz, CDCl₃) δ: 8.15-8.24 (m, 3H), 7.98 (s, 1H), 7.51 (d, J=8.2 Hz, 2H), 7.29 (d, J=8.5 Hz, 1H), 7.08-7.19 (m, 2H), 6.89-7.03 (m, 2H), 5.30 (s, 2H), 4.79 (s, 2H), 2.54 (s, 3H), 2.23 (d, J=5.9 Hz, 6H).

Example 4

Intermediate 4

4-(5-(1-(3,4-dimethylbenzyl)-5-methyl-1H-indol-3-yl)-1,2,4-oxadiazol-3-yl)benzaldehyde

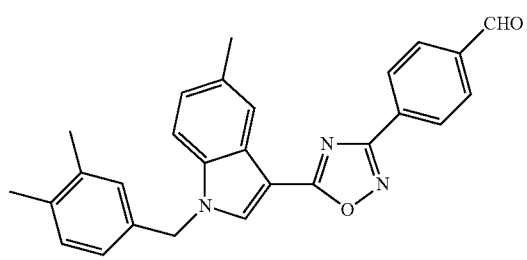 [SMILES: Cc1ccc2c(c1)c(-c1nc(-c3ccc(C=O)cc3)no1)cn2Cc1ccc(C)c(C)c1]

To a solution of Intermediate 3 (300 mg, 0.73 mmol) were added molecular sieves (100 mg), 4-methylmorpholine N-oxide (170 mg, 1.45 mmol) and tetrapropylammonium perruthenate (15 mg, 0.03 mmol). After stirring at room temperature for 45 min the reaction mixture was filtered to remove the tetrapropylammonium perruthenate, concentrated and purified by MPLC using EtOAc and hexane and gave Intermediate 4 (200 mg, 92% yield).

$^1$H NMR (CDCl₃) δ: 10.11 (s, 1H), 8.39 (d, J=8.2 Hz, 2H), 8.17 (s, 1H), 7.92-8.07 (m, 3H), 7.31 (d, J=8.5 Hz, 1H), 7.07-7.20 (m, 2H), 6.87-7.04 (m, 1H), 5.31 (s, 2H), 2.56 (s, 3H), 2.23 (d, 6H).

Example 5

Intermediate 5

(4-(5-(1-benzyl-1H-indol-3-yl)-1,2,4-oxadiazol-3-yl)phenyl)methanol

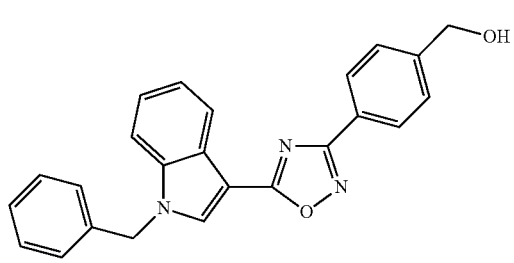 [SMILES: OCc1ccc(-c2noc(-c3cn(Cc4ccccc4)c4ccccc34)n2)cc1]

To a solution of 1H-Indole-3-carboxylic acid, 1-(phenylmethyl) (CAS 27018-76-4) (1.0 g, 4 mmol) in DMF (10 mL) was added CDI (778 mg, 4.3 mmol) at room temperature. The mixture was stirred at room temperature for 30 minutes then (Z)—N'-hydroxy-4-(hydroxymethyl)benzimidamide, (CAS 1233243-49-6) (664 mg, 4 mmol) was added to the reaction mixture at room temperature. The mixture was stirred at room temperature for 16 hrs. After stirring at room temperature for 16 hrs the reaction mixture was transferred into a microwave vial and heated at 150° C. for 20 minutes. The solvent was removed under reduced pressure and gave the crude product. Purification by MPLC using EtOAc and hexane afforded Intermediate 5 (700 mg, 46% yield).

$^1$H NMR (300 MHz, CDCl₃) δ: 8.40 (d, J=7.6 Hz, 1H), 8.17 (d, J=8.2 Hz, 2H), 7.99 (s, 1H), 7.49 (d, J=8.2 Hz, 2H), 7.24-7.41 (m, 3H), 7.13-7.24 (m, 2H), 5.40 (s, 2H), 4.77 (s, 2H).

Example 6

Intermediate 6

4-(5-(1-benzyl-1H-indol-3-yl)-1,2,4-oxadiazol-3-yl)benzaldehyde

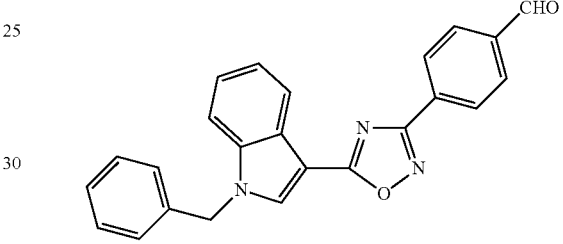

To a solution of Intermediate 5, (700 mg, 1.83 mmol) were added molecular sieves (200 mg), 4-methylmorpholine N-oxide (614 mg, 5.25 mmol) and tetrapropylammonium perruthenate (20 mg). After stirred at room temperature for 40 min and filtered to remove tetrapropylammonium perruthenate, concentrated and purified by MPLC using EtOAc and hexane and gave Intermediate 6 (360 mg, 52% yield).

$^1$H NMR (300 MHz, CDCl₃) δ: 10.11 (s, 1H), 8.31-8.48 (m, 3H), 7.98-8.10 (m, 3H), 7.29-7.45 (m, 3H), 7.16-7.28 (m, 2H), 5.43 (s, 2H).

Example 7

Intermediate 7

1-benzyl-N-(4-(hydroxymethyl)phenyl)-1H-indole-3-carboxamide

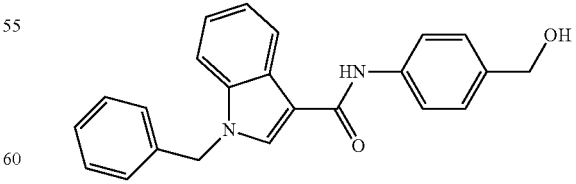

To a solution of 1H-Indole-3-carboxylic acid, 1-(phenylmethyl)-(CAS 27018-76-4) (1.0 g, 3.7 mmol) in DCM (10 mL) was added oxalyl chloride (0.950 mgs, 7.5 mmol) followed by the addition of DMF (3 drops) at room temperature. The solvent was removed under reduced pressure and gave the crude product. To the crude material in DCM (10 mL) was added (4-aminophenyl)methanol, (0.478 mgs, 3.8 mmol), followed by triethylamine (0.98 ml, 7.0 mmol). The reaction mixture was stirred at room temperature overnight. The reaction mixture was quenched with water and extracted in DCM. The organic layer was separated and dried over magnesium sulphate and the solution was filtered. The filtrate was evaporated under reduced pressure to give the crude product, which was purified on a column (MPLC) using DCM:MeOH and gave Intermediate 7 (550 mgs).

$^1$H NMR (300 MHz, CD$_3$OD) δ: 8.48 (s, 1H), 8.51-8.62 (m, 2H), 7.24-7.33 (m, 7H), 7.82 (d, J=8.1 Hz, 2H), 8.95 (d, J=8.1 Hz, 2H), 5.41 (s, 2H), 4.61 (s, 2H).

Example 8

Intermediate 8

1-benzyl-N-(4-formylphenyl)-1H-indole-3-carboxamide

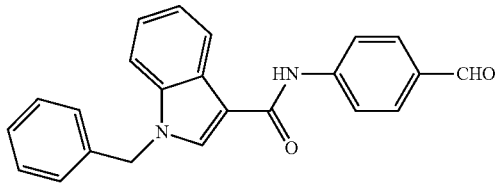 [SMILES: O=Cc1ccc(NC(=O)c2cn(Cc3ccccc3)c3ccccc23)cc1]

To a solution containing Intermediate 7 in acetonitrile (10 mL) was added NMO (400 mgs) followed by the addition of a catalytic amount of TPAP (30 mgs). The reaction material was stirred at room temperature for 2 hours. The crude material was purified on a column (MPLC) using DCM:MeOH and gave Intermediate 8 (505 mgs).

$^1$H NMR (300 MHz, CD$_3$OD) δ: 9.86 (s, 1H), 8.48 (s, 1H), 8.51-8.62 (m, 2H), 7.24-7.33 (m, 7H), 7.82 (d, J=8.1 Hz, 2H), 8.95 (d, J=8.1 Hz, 2H), 5.41 (s, 2H).

Example 9

Intermediate 9

1-(3,4-dimethylbenzyl)-N[4-(hydroxymethyl)phenyl]-5-methyl-1H-indole-3-carboxamide

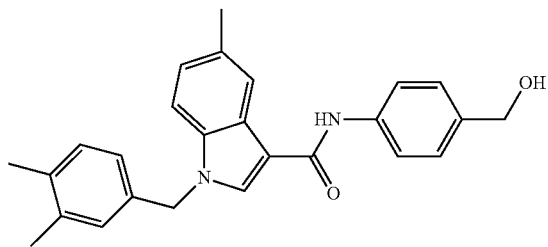 [SMILES: Cc1ccc2c(c1)c(C(=O)Nc1ccc(CO)cc1)cn2Cc1ccc(C)c(C)c1]

To a solution of Intermediate 2 (1.0 g, 3.4 mmol) in DCM (10 mL) was added oxalyl chloride (0.860 mgs, 6.8 mmol) followed by the addition of DMF (3 drops) at room temperature. The solvent was removed under reduced pressure and gave the crude product. To the crude material (1.0 g, 3.5 mmol), in DCM (10 mL) was added (4-aminophenyl)methanol, (0.479 mgs, 3.9 mmol), followed by triethylamine (0.97 ml, 7.0 mmol). The reaction mixture was stirred at room temperature for overnight. The reaction was quenched with water and extracted in CH$_2$Cl$_2$. The organic layer was separated, dried over magnesium sulphate and the solution was filtered. The filtrate was evaporated under reduced pressure to give the crude product, which was purified on a column (MPLC) using CH$_2$Cl$_2$:MeOH and gave Intermediate 9 (600 mgs).

$^1$H NMR (300 MHz, CD$_3$OD) δ: 8.43 (s, 1H), 8.56-8.68 (m, 2H), 7.24-7.33 (m, 4H), 7.72 (d, J=8.1 Hz, 2H), 8.72 (d, J=8.1 Hz, 2H), 5.51 (s, 2H), 4.69 (s, 2H), 2.38 (s, 6H), 2.32 (s, 3H).

Example 10

Intermediate 10

1-(3,4-dimethylbenzyl)-N-(4-formylphenyl)-5-methyl-1H-indole-3-carboxamide

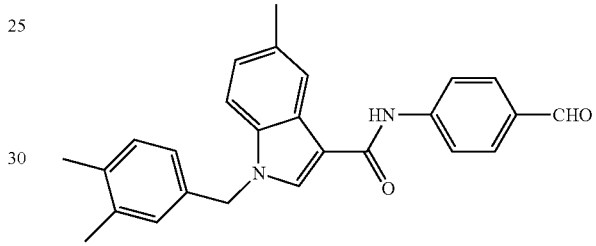

To a solution containing (600 mgs, 1.50 mmol) Intermediate 9 in acetonitrile (10 mL) was added NMO (440 mgs, 3.76 mmol) followed by the addition of a catalytic amount of TPAP (30 mgs). The reaction material was stirred at room temperature for 2 hours. The crude material was purified on a column (MPLC) using CH$_2$Cl$_2$:MeOH and gave Intermediate 10 (555 mgs).

$^1$H NMR (300 MHz, CD$_3$OD) δ: $^1$H NMR (300 MHz, CD$_3$OD) δ: 9.46 (s, 1H), 8.44 (s, 1H), 8.62-8.68 (m, 2H), 7.27-7.35 (m, 4H), 7.72 (d, J=8.1 Hz, 2H), 8.72 (d, J=8.1 Hz, 2H), 5.51 (s, 2H), 2.36 (s, 6H), 2.30 (s, 3H).

Example 11

Compound 1

1-(4-{5-[1-(3,4-dimethylbenzyl)-5-methyl-1H-indol-3-yl]-1,2,4-oxadiazol-3-yl}benzyl)azetidine-3-carboxylic acid

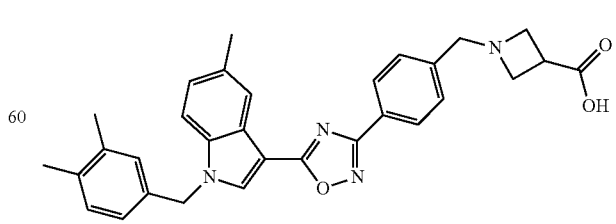

Azetidine-3-carboxylic acid (CAS 36476-78-5) (37 mg, 0.37 mmol) was added to a solution of Intermediate 2 (100 mg, 0.243 mmol) in MeOH (10 mL) and DCM (5 mL) followed by AcOH (2 drops) at room temperature. The reaction mixture was stirred at room temperature for 20 minutes then NaCNBH$_3$ (15 mg, 0.243 mmol) was added to the reaction mixture in 2 mL MeOH. The reaction mixture was stirred at room temperature for another 2 h. The reaction mixture was then quenched with water (1 mL) and silica gel was added, concentrated to dryness, then purified on a column (MPLC) using DCM:MeOH and gave Compound 1 (41 mg).

$^1$NMR (300 MHz, CD$_3$OD) δ: 8.13-8.24 (m, 3H), 8.07 (s, 1H), 7.80 (s, 1H), 7.58 (d, J=8.2 Hz, 2H), 7.37 (d, J=8.5 Hz, 1H), 6.92-7.19 (m, 3H), 5.38 (s, 2H), 4.22 (s, 2H), 3.87-4.10 (m, 4H), 3.34-3.39 (s, 1H), 2.52 (s, 3H), 2.22 (d, J=1.8 Hz, 6H).

Compounds 2 through 9 were prepared from the corresponding starting materials in a similar manner to the procedure described in Example 11 for Compound 1. The results are tabulated below in Table 1.

TABLE 1

| Comp. No. | IUPAC name | Starting material | $^1$H NMR δ (ppm) |
|---|---|---|---|
| 2 | 1-(4-{5-[1-(3,4-dimethylbenzyl)-5-fluoro-1H-indol-3-yl]-1,2,4-oxadiazol-3 yl}benzyl)azetidine-3-carboxylic acid | 1H-Indole-3-carboxylic acid, 5-fluoro-, methyl ester (CAS 310886-79-4) | $^1$H NMR (300 MHz, CD$_3$OD) δ: 8.33 (s, 1H), 8.22 (d, J = 7.6 Hz, 2H), 7.93 (d, J = 8.8 Hz, 1H), 7.61 (d, J = 7.9 Hz, 2H), 7.43-7.54 (m, 1H), 7.08 (d, J = 5.0 Hz, 4H), 5.43 (s, 2H), 4.29 (s, 2H), 3.96-4.17 (m, 4H), 3.36-3.42 (m, 1H), 2.22 (s, 6H) |
| 3 | 1-(4-{5-[1-(3,4-dimethylbenzyl)-5-methoxy-2-methyl-1H-indol-3-yl]-1,2,4-oxadiazol-3-yl}benzyl)azetidine-3-carboxylic acid | 1H-Indole-3-carboxylic acid, 5-methoxy-2-methyl-, methyl ester (CAS 4871-80-1) | $^1$H NMR (CD$_3$OD, 300 MHz) δ: 8.24 (d, J = 8.5 Hz, 2H), 7.79 (d, J = 2.3 Hz, 1H), 7.62 (d, J = 7.9 Hz, 2H), 7.33 (d, J = 8.8 Hz, 1H), 7.04 (d, J = 8.5 Hz, 1H), 6.80-6.93 (m, 2H), 6.74 (d, J = 7.6 Hz, 1H), 5.43 (s, 2H), 4.36 (s, 2H), 4.09-4.19 (m, 4H), 3.91 (s, 3H), 3.35-3.46 (m, 1H), 2.87 (s, 3H), 2.19 (d, 6H). |
| 4 | 1-(4-{5-[1-(3,4-dimethylbenzyl)-1H-indol-3-yl]-1,2,4-oxadiazol-3-yl}benzyl)azetidine-3-carboxylic acid | 1H-Indole-3-carboxylic acid, methyl ester (CAS 942-24-5) | $^1$H NMR (CD$_3$OD, 300 MHz) δ: 8.17-8.33 (m, 4H), 7.62 (d, J = 8.2 Hz, 2H), 7.50 (dd, J = 6.0, 2.5 Hz, 1H), 7.25-7.35 (m, 2H), 7.04-7.11 (m, 2H), 6.93-7.01 (m, 1H), 5.43 (s, 2H), 4.38 (s, 2H), 4.16 (d, J = 8.5 Hz, 4H), 3.41 (t, J = 8.1 Hz, 1H), 2.21 (s, 6H) |

TABLE 1-continued

| Comp. No. | IUPAC name | Starting material | $^1$H NMR δ (ppm) |
|---|---|---|---|
| 5 | 1-{4-[5-(1-benzyl-5-fluoro-1H-indol-3-yl]-1,2,4-oxadiazol-3-yl]benzyl}azetidine-3-carboxylic acid | 1H-Indole-3-carboxylic acid, 5-fluoro-, methyl ester (CAS 310886-79-4) | $^1$H NMR (CD$_3$OD, 300 MHz) δ: 8.40 (s, 1H), 8.20-8.29 (m, 2H), 7.89-7.98 (m, 1H), 7.59-7.67 (m, 2H), 7.52 (d, J = 14.1 Hz, 1H), 7.22-7.39 (m, 4H), 7.02-7.12 (m, 2H), 5.54 (s, 2H), 4.36 (s, 2H), 4.16 (d, J = 7.6 Hz, 4H), 3.41 (t, J = 8.1 Hz, 1H). |
| 6 | 1-benzyl-3-{3-[4-(1H-imidazol-1-ylmethyl)phenyl]-1,2,4-oxadiazol-5-yl}-1H-indole | 1H-Indole-3-carboxylic acid, methyl ester (CAS 942-24-5) (Z)-4-((1H-imidazol-1-yl)methyl)-N'-hydroxy-benzimidamide (CAS 1016774-72-3) | $^1$H NMR (300 MHz, CDCl$_3$) δ: 8.36-8.47 (m, 1H), 8.19 (d, J = 8.2 Hz, 2H), 8.04 (s, 1H), 7.63 (s, 1H), 7.08-7.47 (m, 10H), 6.94 (s, 1H), 5.42 (s, 2H), 5.21 (s, 2H) |
| 7 | 1-(3,4-dimethylbenzyl)-5-fluoro-3-{3-[4-(1H-imidazol-1-ylmethyl)phenyl]-1,2,4-oxadiazol-5-yl}-1H-indole | 1H-Indole-3-carboxylic acid, 5-fluoro-, methyl ester (CAS 310886-79-4) (Z)-4-((1H-imidazol-1-yl)methyl)-N'-hydroxy-benzimidamide (CAS 1016774-72-3) | $^1$H NMR (CD$_3$OD, 300 MHz) δ: 8.28 (s, 1H), 8.13 (d, J = 8.2 Hz, 2H), 7.89 (dd, J = 9.4, 2.3 Hz, 1H), 7.80 (s, 1H), 7.46 (dd, J = 8.9, 4.2 Hz, 1H), 7.39 (d, J = 8.2 Hz, 2H), 7.16 (s, 1H), 6.92-7.11 (m, 5H), 5.40 (s, 2H), 5.31 (s, 2H), 2.21 (s, 6H) |

TABLE 1-continued

| Comp. No. | IUPAC name | Starting material | $^1$H NMR δ (ppm) |
|---|---|---|---|
| 8 | 3-({4-[5-(1-benzyl-1H-indol-3-yl)-1,2,4-oxadiazol-3-yl]benzyl}amino)propanoic acid | Intermediate 6 | $^1$H NMR (300 MHz, CDCl$_3$) δ: 8.23-8.38 (m, 2H), 8.11 (d, J = 8.2 Hz, 2H), 7.48 (d, J = 7.9 Hz, 3H), 7.19-7.42 (m, 7H), 5.54 (s, 2H), 3.71 (s, 2H), 3.50-3.63 (m, 2H), 3.14-3.45 (m, 3H) |
| 9 | 1-{4-[5-[1-(3,4-dimethylbenzyl)-5-fluoro-2-methyl-1H-indol-3-yl]-1,2,4-oxadiazol-3-yl]benzyl)azetidine-3-carboxylic acid | 1H-Indole-3-carboxylic acid, 5-fluoro-2-methyl- (CAS 98621-77-3) | $^1$H NMR (CD$_3$OD, 300 MHz) δ: 8.19-8.28 (m, 2H), 7.93 (dd, J = 9.1, 2.1 Hz, 2H), 7.62 (d, J = 8.2 Hz, 2H), 7.38-7.45 (m, 1H), 6.95-7.13 (m, 2H), 6.86 (s, 1H), 5.45 (s, 2H), 4.38 (s, 2H), 4.16 (d, J = 8.2 Hz, 4H), 3.41 (t, J = 8.6 Hz, 1H), 2.88 (s, 3H), 2.19 (d, J = 6.4 Hz, 6H) |

Example 12

Compound 10

3-[5-(1-benzyl-1H-indol-3-yl)-1,2,4-oxadiazol-3-yl]-N-methylpyridin-2-amine

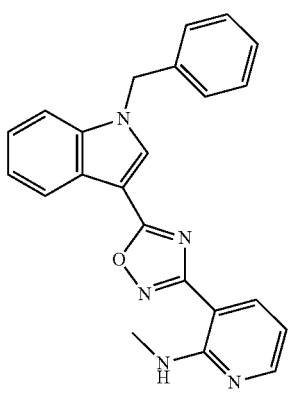 [SMILES: CNc1ncccc1-c1noc(-c2cn(Cc3ccccc3)c3ccccc23)n1]

To a solution of 1H-Indole-3-carboxylic acid, 1-(phenylmethyl) (CAS 27018-76-4) (210 mg, 0.836 mmol) in DMF (5 mL) was added CDI (162 mg, 1 mmol) at room temperature. The mixture was stirred at room temperature for 30 minutes then 3-Pyridinecarboximidamide, N-hydroxy-2-(methylamino) (CAS 801303-19-5) (139 mg, 0.836 mmol) was added to the reaction mixture. The mixture was stirred at room temperature for 16 hrs. Then reaction mixture was transferred into a microwave vial and heated at 150° C. for 20 minutes. The solvent was removed under reduced pressure and gave the crude product. Purification by MPLC using EtOAc and hexane afforded Compound 10 (50 mg).

$^1$HNMR (CD$_3$OD, 300 MHz) δ: 8.48 (dd, J=7.3, 1.8 Hz, 1H), 8.34 (s, 1H), 8.28 (dd, J=7.6, 1.5 Hz, 1H), 8.19-8.25 (m, 1H), 7.45-7.55 (m, 1H), 7.22-7.38 (m, 7H), 6.77 (dd, J=7.6, 5.0 Hz, 1H), 5.54 (s, 2H), 3.13 (s, 3H).

Compound 11 was prepared from the corresponding starting materials in a similar manner to the procedure described in Example 12 for Compound 10. The results are tabulated below in Table 2.

TABLE 2

| Comp. No. | IUPAC name | Starting material | $^1$H NMR δ (ppm) |
|---|---|---|---|
| 11 | 3-{5-[1-(3,4-dimethylbenzyl)-5-fluoro-1H-indol-3-yl]-1,2,4-oxadiazol-3-yl}-N-methylpyridin-2-amine | 1H-Indole-3-carboxylic acid, 5-fluoro-, methyl ester (CAS 310886-79-4) | $^1$H NMR (CDCl$_3$, 300 MHz) δ: 7.83-7.98 (m, 3H), 7.23 (d, J = 4.4 Hz, 1H), 7.10 (d, J = 7.9 Hz, 1H), 6.79-7.05 (m, 4H), 5.25 (s, 2H), 2.23 (d, J = 5.0 Hz, 3H) |

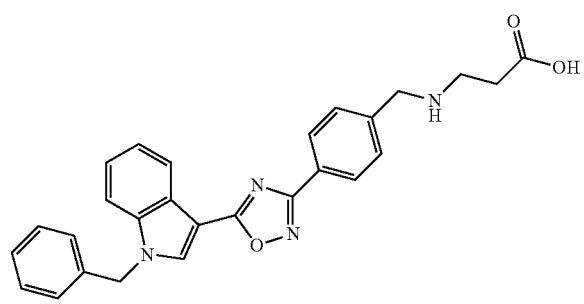 [SMILES: O=C(O)CCNCc1ccc(-c2noc(-c3cn(Cc4ccccc4)c4ccccc34)n2)cc1]

Example 13

Compound 12

3-({4-[5-(1-benzyl-1H-indol-3-yl)-1,2,4-oxadiazol-3-yl]benzyl}amino)propanoic acid 3-aminopropanoic acid (42 mg, 0.47 mmol) was added to a solution of Intermediate 6 (108 mg, 0.312 mmol) in MeOH (10 mL) followed by AcOH (2 drops) at room temperature. The reaction mixture was stirred at room temperature for 20 minutes then NaCNBH$_3$ (20 mg, 0.312 mmol) was added to the reaction mixture in 2 mL MeOH. The reaction mixture was stirred at room temperature for another 2 h. The reaction mixture was then quenched with water (1 mL) and silica gel was added, then concentrated to dryness, and purified on a column (MPLC) using DCM:MeOH and gave Compound 12 (17 mg).

$^1$H NMR (CD$_3$OD, 300 MHz) δ: 8.18-8.40 (m, 4H), 7.66-7.70 (m, 2H), 7.48-7.55 (m, 1H), 7.22-7.39 (m, 6H), 5.56 (s, 2H), 4.28 (s, 2H), 3.14-3.24 (m, 2H), 2.49-2.55 (m, 2H).

Compounds 13 through 17 were prepared from the corresponding starting materials in a similar manner to the procedure described in Example 13 for Compound 12. The results are tabulated below in Table 3.

TABLE 3

| Comp. No. | IUPAC name | Starting material | $^1$H NMR δ (ppm) |
|---|---|---|---|
| 13 | 3-[(4-{5-[1-(3,4-dimethylbenzyl)-5-methyl-1H-indol-3-yl]-1,2,4-oxadiazol-3-yl}benzyl)amino]propanoic acid | Intermediate 4 | |

TABLE 3-continued

| Comp. No. | IUPAC name | Starting material | $^1$H NMR δ (ppm) |
|---|---|---|---|
| 14 | 3-[(4-{5-[1-(3,4-dimethylbenzyl)-5-fluoro-1H-indol-3-yl]-1,2,4-oxadiazol-3-yl}benzyl)amino]propanoic acid | 1H-Indole-3-carboxylic acid, 5-fluoro-methyl ester (CAS 310886-79-4) NMO | $^1$H NMR (300 MHz, CDCl$_3$) δ: 8.13 (d, J = 7.9 Hz, 2H), 7.94 (d, J = 2.9 Hz, 2H), 7.56 (d, J = 7.9 Hz, 2H), 7.22 (dd, J = 8.9, 4.2 Hz, 1H), 7.09 (d, J = 7.6 Hz, 1H), 6.85-7.03 (m, 3H), 5.21 (s, 2H), 4.10 (s, 2H), 3.01-3.06 (m, 2H), 2.49-2.65 (m, 1H), 2.21 (d, 6H). |
| 15 | 5-({4-[5-(1-benzyl-1H-indol-3-yl)-1,2,4-oxadiazol-3-yl]benzyl}amino)pentanoic acid | Intermediate 8 | $^1$H NMR (CD$_3$OD, 300 MHz) δ: 8.30 (s, 2H), 8.12 (d, J = 8.2 Hz, 2H), 7.54 (d, J = 7.9 Hz, 2H), 7.22-7.40 (m, 7H), 5.51 (s, 2H), 3.86 (s, 2H), 2.60-2.76 (m, 2H), 2.12-2.28 (m, 2H), 1.53-1.73 (m, 4H). |
| 16 | 3-[(4-{5-[1-(3,4-dimethylbenzyl)-1H-indol-3-yl]-1,2,4-oxadiazol-3-yl}benzyl)amino]pentanoic acid | 1H-Indole-3-carboxylic acid, methyl ester (CAS 942-24-5) NMO | $^1$H NMR (CD$_3$OD, 300 MHz) δ: 8.20-8.33 (m, 4H), 7.67 (d, J = 7.6 Hz, 2H), 7.52 (d, J = 7.0 Hz, 1H), 7.27-7.36 (m, 2H), 7.04-7.14 (m, 2H), 6.95-7.02 (m, 1H), 5.44 (s, 2H), 4.28 (s, 2H), 3.14-3.23 (m, 2H), 2.47-2.56 (m, 2H), 2.21 (s, 6H) |

TABLE 3-continued

| Comp. No. | IUPAC name | Starting material | $^1$H NMR δ (ppm) |
|---|---|---|---|
| 17 | 3-({4-[5-(1-benzyl-5-fluoro-1H-indol-3-yl)-1,2,4-oxadiazol-3-yl]benzyl}amino)propanoic acid | 1H-Indole-3-carboxylic acid, 5-fluoro-, methyl ester (CAS 310886-79-4) NMO | $^1$H NMR (CD$_3$OD, 300 MHz) δ: 8.37 (s, 1H), 8.24 (d, J = 7.9 Hz, 2H), 7.89-7.97 (m, 1H), 7.68 (d, J = 8.2 Hz, 2H), 7.44-7.53 (m, 1H), 7.21-7.39 (m, 5H), 7.07 (d, J = 2.1 Hz, 1H), 5.52 (s, 2H), 4.30 (s, 2H), 3.22 (t, J = 6.6 Hz, 2H), 2.53 (t, 2H). |

Example 14

Compound 18

1-{4-[(1-Benzyl-1H-indole-3-carbonyl)-amino]-benzyl}-azetidine-3-carboxylic

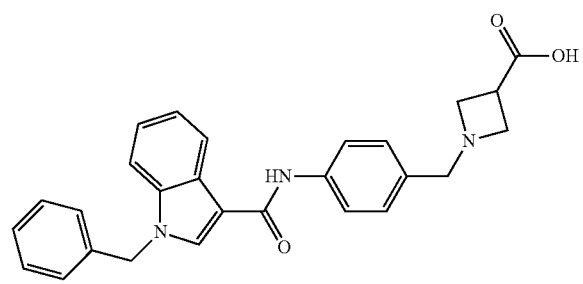 [SMILES: O=C(Nc1ccc(CN2CC(C(=O)O)C2)cc1)c1cn(Cc2ccccc2)c2ccccc12]

Azetidine-3-carboxylic acid (25 mg, 0.251 mmol) was added to a solution of Intermediate 8 (100 mg, 0.251 mmol) in MeOH (10 mL) followed by AcOH (2 drops) at room temperature. The reaction mixture was stirred at room temperature for 20 minutes then NaCNBH$_3$ (16 mg, 0.251 mmol) was added to the reaction mixture in 2 mL MeOH. The reaction mixture was stirred at room temperature for 2 h. The reaction mixture was quenched with water (1 mL) and silica gel was added, then concentrated to dryness, and purified on a column (MPLC) using DCM:MeOH and gave Compound 18 (46 mg).

$^1$H NMR (300 MHz, CD$_3$OD) δ: 8.13 (s, 1H), 8.17-8.27 (m, 2H), 7.64 (d, J=8.5 Hz, 2H), 7.37-7.45 (m, 1H), 7.12-7.37 (m, 8H), 5.46 (s, 2H), 3.64 (s, 2H), 3.57 (t, J=8.4 Hz, 2H), 3.33-3.44 (m, 2H), 3.02-3.26 (m, 1H).

Compounds 19 and 20 were prepared from the corresponding starting materials in a similar manner to the procedure described in Example 14 for Compound 18. The results are tabulated below in Table 4.

TABLE 4

| Comp. No. | IUPAC name | Starting material | $^1$H NMR δ (ppm) |
|---|---|---|---|
| 19 | 1-(4-(1-(3,4-dimethylbenzyl)-5-fluoro-1H-indole-3-carboxamido)benzyl)azetidine-3-carboxylic acid | 1H-Indole-3-carboxylic acid, 5-fluoro-, methyl ester (CAS 310886-79-4) | $^1$H NMR (300 MHz, CD$_3$OD) δ: 8.43 (s, 1H), 7.72-7.91 (m, 2H), 7.61 (d, J = 8.4 Hz, 2H), 7.37-7.49 (m, 3H), 6.81-7.12 (m, 3H), 5.41 (s, 2H), 3.71 (s, 2H), 3.62 (t, J = 8.4 Hz, 2H), 3.52 (t, J = 8.4 Hz, 2H), 3.06-3.21 (m, 1H), 2.34 (s, 6H). |

TABLE 4-continued

| Comp. No. | IUPAC name | Starting material | $^1$H NMR δ (ppm) |
|---|---|---|---|
| 20 | 1-(4-{[1-(3,4-Dimethyl-benzyl)-5-meenzyl)-azetidine-3-carboxylic acid | Intermediate 1 | $^1$H NMR (300 MHz, CD$_3$OD) δ: 8.41 (s, 1H), 7.69-7.82 (m, 2H), 7.66 (d, J = 8.4 Hz, 2H), 7.32-7.44 (m, 3H), 6.75-7.01 (m, 3H), 5.40 (s, 2H), 3.69 (s, 2H), 3.66 (t, J = 8.4 Hz, 2H), 3.52 (t, J = 8.4 Hz, 2H), 2.96-3.11 (m, 1H), 2.34 (s, 6H), 2.12 (s, 3H). |

Example 15

Compound 21

3-(4-{[1-(3,4-Dimethyl-benzyl)-5-methyl-1H-indole-3-carbonyl]-amino}-benzylamino)-propionic acid

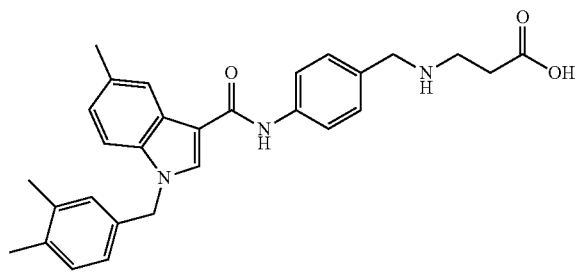 [SMILES: Cc1ccc2c(c1)c(C(=O)Nc1ccc(CNCCC(=O)O)cc1)cn2Cc1ccc(C)c(C)c1]

3-aminopropanoic acid (25 mg, 0.251 mmol) was added to a solution of Intermediate 10 (100 mg, 0.251 mmol) in MeOH (10 mL) followed by AcOH (2 drops) at room temperature. The reaction mixture was stirred at room temperature for 20 minutes then NaCNBH$_3$ (16 mg, 0.251 mmol) was added to the reaction mixture in 2 mL MeOH. The reaction mixture was stirred at room temperature for 2 h. The reaction mixture was then quenched with water (1 mL) and silica gel was added, concentrated to dryness, then purified on a column (MPLC) using CH$_2$Cl$_2$:MeOH and gave Compound 21 (21 mg).

$^1$H NMR (300 MHz, CD$_3$OD) δ: 8.43 (s, 1H), 7.61-7.78 (m, 2H), 7.61 (d, J=8.4 Hz, 2H), 7.36-7.49 (m, 3H), 6.75-7.04 (m, 3H), 5.42 (s, 2H), 3.78 (s, 2H), 3.59-3.71 (m, 2H), 3.42-3.51 (m, 2H), 2.41 (s, 6H), 2.07 (s, 3H).

Compound 22 was prepared from the corresponding starting materials in a similar manner to the procedure described in Example 15 for Compound 21. The results are tabulated below in Table 5.

TABLE 5

| Comp. No. | IUPAC name | Starting material | $^1$H NMR δ (ppm) |
|---|---|---|---|
| 22 | 3-(4-{[1-(3,4-Dimethyl-benzyl)-5-fluoro-1H-indole-3-carbonyl]-amino}-benzylamino)-propionic acid | 1H-Indole-3-carboxylic acid, 5-fluoro-, methyl ester (CAS 310886-79-4) | $^1$H NMR (300 MHz, CD$_3$OD) δ: 8.43 (s, 1H), 7.72-7.91 (m, 2H), 7.55 (d, J = 8.4 Hz, 2H), 7.34-7.41 (m, 3H), 6.78-7.09 (m, 3H), 5.39 (s, 2H), 3.69 (s, 2H), 3.52-3.61 (m, 2H), 3.42-3.49 (m, 2H), 2.34 (s, 6H). |

GTP γ³⁵S Binding Assay

The S1P1 activity of the compounds according to the invention, were tested using the GTP $\gamma^{35}$S binding assay. The compounds were assessed for their ability to activate or block activation of the human S1P1 receptor in cells stably expressing the S1P1 receptor.

GTP $\gamma^{35}$S binding was measured in the medium containing (mM) HEPES 25, pH 7.4, MgCl$_2$ 10, NaCl 100, dithitothreitol 0.5, digitonin 0.003%, 0.2 nM GTP $\gamma^{35}$S, and 5 µg membrane protein in a volume of 150 µl. Test compounds were included in the concentration range from 0.08 to 5,000 nM unless indicated otherwise. Membranes were incubated with 100 µM 5'-adenylylimmidodiphosphate for 30 min, and subsequently with 10 µM GDP for 10 min on ice. Drug solutions and membrane were mixed, and then reactions were initiated by adding GTP $\gamma^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP $\gamma^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Activity potency: S1P1 receptor from GTP$\gamma^{35}$S: nM, (EC$_{50}$), % stimulation,

TABLE 6

| IUPAC name | S1P1 EC$_{50}$ nM | % stimulation |
|---|---|---|
| 1-{4-[5-(1-benzyl-1H-indol-3-yl)-1,2,4-oxadiazol-3-yl]benzyl}azetidine-3-carboxylic acid | 494 | 0.66 |
| 3-({4-[5-(1-benzyl-1H-indol-3-yl)-1,2,4-oxadiazol-3-yl]benzyl}amino)propanoic acid | 394 | 0.89 |
| 1-(4-{5-[1-(3,4-dimethylbenzyl)-5-fluoro-1H-indol-3-yl]-1,2,4-oxadiazol-3-yl}benzyl)azetidine-3-carboxylic acid | 737 | 0.94 |
| 3-[(4-{5-[1-(3,4-dimethylbenzyl)-5-fluoro-1H-indol-3-yl]-1,2,4-oxadiazol-3-yl}benzyl)amino]propanoic acid | 1493 | 0.93 |
| 1-(4-{5-[1-(3,4-dimethylbenzyl)-5-methyl-1H-indol-3-yl]-1,2,4-oxadiazol-3-yl}benzyl)azetidine-3-carboxylic acid | 426 | 0.92 |
| 3-[(4-{5-[1-(3,4-dimethylbenzyl)-5-methyl-1H-indol-3-yl]-1,2,4-oxadiazol-3-yl}benzyl)amino]propanoic acid | 351 | 0.82 |
| 1-benzyl-3-{3-[4-(1H-imidazol-1-ylmethyl)phenyl]-1,2,4-oxadiazol-5-yl}-1H-indole | 1157 | 0.86 |
| 3-[5-(1-benzyl-1H-indol-3-yl)-1,2,4-oxadiazol-3-yl]-N-methylpyridin-2-amine | 703 | 0.88 |
| 3-({4-[5-(1-benzyl-1H-indol-3-yl)-1,2,4-oxadiazol-3-yl]benzyl}amino)propanoic acid | 394 | 1.08 |
| 5-({4-[5-(1-benzyl-1H-indol-3-yl)-1,2,4-oxadiazol-3-yl]benzyl}amino)pentanoic acid | 1012 | 1.08 |
| 3-{5-[1-(3,4-dimethylbenzyl)-5-fluoro-1H-indol-3-yl]-1,2,4-oxadiazol-3-yl}-N-methylpyridin-2-amine | 569 | — |
| 1-(4-{5-[1-(3,4-dimethylbenzyl)-5-fluoro-2-methyl-1H-indol-3-yl]-1,2,4-oxadiazol-3-yl}benzyl)azetidine-3-carboxylic acid | 1003 | 0.85 |
| 1-(4-{5-[1-(3,4-dimethylbenzyl)-5-methoxy-2-methyl-1H-indol-3-yl]-1,2,4-oxadiazol-3-yl}benzyl)azetidine-3-carboxylic acid | 1556 | 0.82 |
| 1-(4-{5-[1-(3,4-dimethylbenzyl)-1H-indol-3-yl]-1,2,4-oxadiazol-3-yl}benzyl)azetidine-3-carboxylic acid | 1015 | 0.92 |

TABLE 6-continued

| IUPAC name | S1P1 EC$_{50}$ nM | % stimulation |
|---|---|---|
| 3-[(4-{5-[1-(3,4-dimethylbenzyl)-1H-indol-3-yl]-1,2,4-oxadiazol-3-yl}benzyl)amino]propanoic acid | 1443 | 0.81 |
| 1-{4-[5-(1-benzyl-5-fluoro-1H-indol-3-yl)-1,2,4-oxadiazol-3-yl]benzyl}azetidine-3-carboxylic acid | 189 | 0.91 |
| 3-({4-[5-(1-benzyl-5-fluoro-1H-indol-3-yl)-1,2,4-oxadiazol-3-yl]benzyl}amino)propanoic acid | 129 | 1.00 |

What is claimed is:

1. A compound of Formula II or its enantiomers, diastereoisomers, tautomers or a pharmaceutically acceptable salt thereof

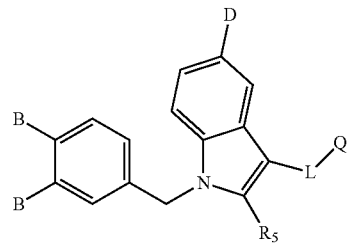

Formula II wherein:

B is the same or is independently C$_{1-4}$ alkyl, methoxy, hydrogen, hydroxyl, halogen, nitrile, trifluoromethyl, amino, carboxylic acid or alkoxy;

D is C$_{1-4}$ alkyl, methoxy, hydrogen, hydroxyl, halogen, nitrile, trifluoromethyl, amino or carboxylic acid;

L is

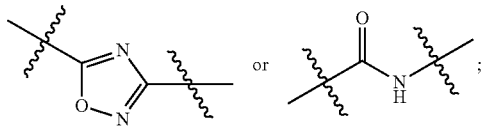 [SMILES: *c1noc(*)n1 ; *NC(*)=O]

Q is one of the following structures:

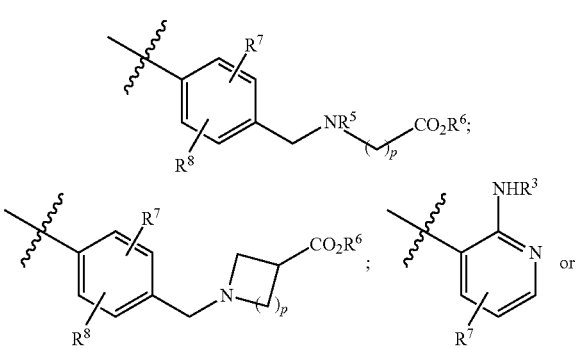

-continued

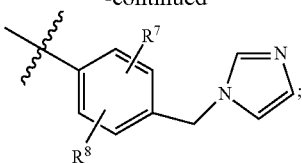

$R^3$ is $C_{1-3}$ alkyl;
$R^5$ is H or Methyl;
$R^6$ is H or Methyl;
p is 1, 2, 3 or 4;
$R_7$ is H, $C_{1-10}$ alkyl, aminoalkyl, halogen, nitrile or trifluoromethyl;
$R_8$ is H, $C_{1-10}$ alkyl, aminoalkyl, halogen, nitrile or trifluoromethyl.

2. A compound according to claim 1 wherein:
L is

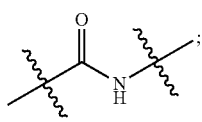 [SMILES: *NC(*)=O]

and
Q is one of the following structures:

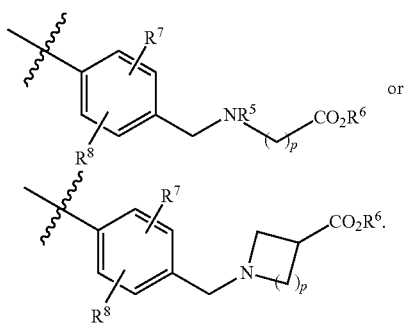

3. A compound according to claim 2 wherein:
L is

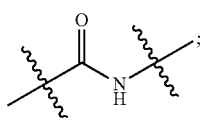 [SMILES: *NC(*)=O]

and
Q is

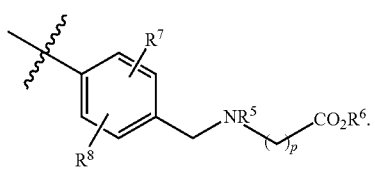

4. A compound according to claim 2 wherein:
L is

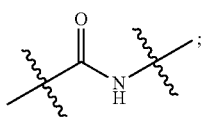 [SMILES: *NC(*)=O]

and
Q is

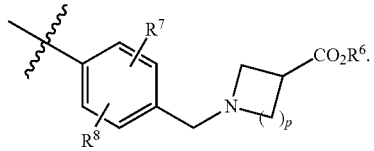

5. A compound according to claim 1 wherein:
L is

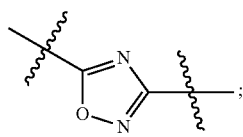 [SMILES: *c1noc(*)n1]

and
Q is one of the following structures:

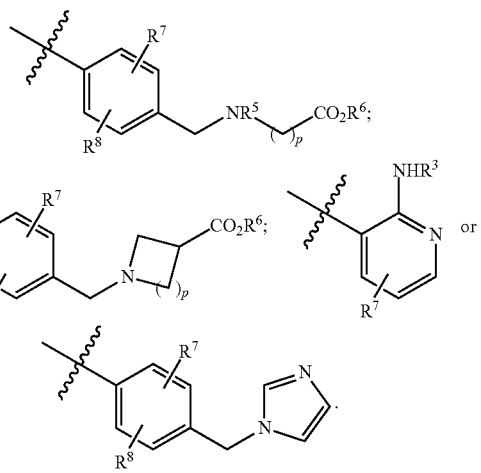

6. A compound according to claim 5 wherein:
L is

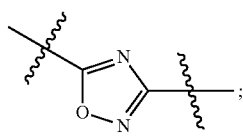 [SMILES: *c1noc(*)n1]

and
Q is:

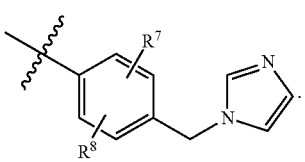

7. A compound according to claim 5 wherein:
L is

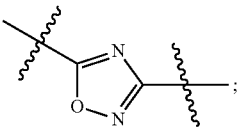 [SMILES: *c1noc(*)n1]

and
Q is

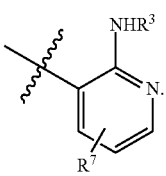

8. A compound according to claim 5 wherein:
L is

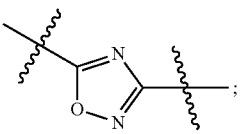

and
Q is

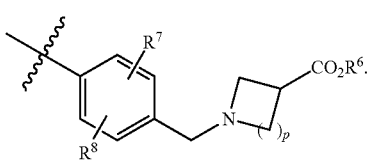

9. A compound according to claim 5 wherein:
L is

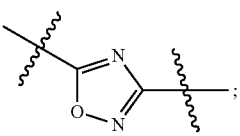 [SMILES: *c1noc(*)n1]

and
Q is

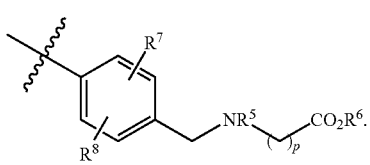

10. A compound according to claim 1 selected from:
3-[(4-{5-[1-(3,4-dimethylbenzyl)-5-methyl-1H-indol-3-yl]-1,2,4-oxadiazol-3-yl}benzyl)amino]propanoic acid;
1-{4-[5-(1-benzyl-5-fluoro-1H-indol-3-yl)-1,2,4-oxadiazol-3-yl]benzyl}azetidine-3-carboxylic acid;
1-(4-{5-[1-(3,4-dimethylbenzyl)-5-methoxy-2-methyl-1H-indol-3-yl]-1,2,4-oxadiazol-3-yl}benzyl)azetidine-3-carboxylic acid;
3-[(4-{5-[1-(3,4-dimethylbenzyl)-5-fluoro-1H-indol-3-yl]-1,2,4-oxadiazol-3-yl}benzyl)amino]propanoic acid;
1-benzyl-3-{3-[4-(1H-imidazol-1-ylmethyl)phenyl]-1,2,4-oxadiazol-5-yl}-1H-indole;
3-({4-[5-(1-benzyl-5-fluoro-1H-indol-3-yl)-1,2,4-oxadiazol-3-yl]benzyl}amino)propanoic acid;
1-{4-[5-(1-benzyl-1H-indol-3-yl)-1,2,4-oxadiazol-3-yl]benzyl}azetidine-3-carboxylic acid;
3-[5-(1-benzyl-1H-indol-3-yl)-1,2,4-oxadiazol-3-yl]-N-methylpyridin-2-amine;
1-(3,4-dimethylbenzyl)-5-fluoro-3-{3-[4-(1H-imidazol-1-ylmethyl)phenyl]-1,2,4-oxadiazol-5-yl}-1H-indole;
1-(4-{5-[1-(3,4-dimethylbenzyl)-5-fluoro-1H-indol-3-yl]-1,2,4-oxadiazol-3-yl}benzyl)azetidine-3-carboxylic acid;
1-(4-{5-[1-(3,4-dimethylbenzyl)-5-fluoro-2-methyl-1H-indol-3-yl]-1,2,4-oxadiazol-3-yl}benzyl)azetidine-3-carboxylic acid;
3-({4-[5-(1-benzyl-1H-indol-3-yl)-1,2,4-oxadiazol-3-yl]benzyl}amino)propanoic acid;
3-{5-[1-(3,4-dimethylbenzyl)-5-fluoro-1H-indol-3-yl]-1,2,4-oxadiazol-3-yl}-N-methylpyridin-2-amine;
1-(4-{5-[1-(3,4-dimethylbenzyl)-1H-indol-3-yl]-1,2,4-oxadiazol-3-yl}benzyl)azetidine-3-carboxylic acid;
3-[(4-{5-[1-(3,4-dimethylbenzyl)-1H-indol-3-yl]-1,2,4-oxadiazol-3-yl}benzyl)amino]propanoic acid;
1-(4-{5-[1-(3,4-dimethylbenzyl)-5-methyl-1H-indol-3-yl]-1,2,4-oxadiazol-3-yl}benzyl)azetidine-3-carboxylic acid; and
5-({4-[5-(1-benzyl-1H-indol-3-yl)-1,2,4-oxadiazol-3-yl]benzyl}amino)pentanoic acid.

11. A pharmaceutical composition comprising as active ingredient a compound according to claim 1 and a pharmaceutically acceptable adjuvant, diluent or carrier.

12. A pharmaceutical composition according to claim 11 wherein the compound is selected from:
3-[(4-{5-[1-(3,4-dimethylbenzyl)-5-methyl-1H-indol-3-yl]-1,2,4-oxadiazol-3-yl}benzyl)amino]propanoic acid;
1-{4-[5-(1-benzyl-5-fluoro-1H-indol-3-yl)-1,2,4-oxadiazol-3-yl]benzyl}azetidine-3-carboxylic acid;
1-(4-{5-[1-(3,4-dimethylbenzyl)-5-methoxy-2-methyl-1H-indol-3-yl]-1,2,4-oxadiazol-3-yl}benzyl)azetidine-3-carboxylic acid;
3-[(4-{5-[1-(3,4-dimethylbenzyl)-5-fluoro-1H-indol-3-yl]-1,2,4-oxadiazol-3-yl}benzyl)amino]propanoic acid;
1-benzyl-3-{3-[4-(1H-imidazol-1-ylmethyl)phenyl]-1,2,4-oxadiazol-5-yl}-1H-indole;
3-({4-[5-(1-benzyl-5-fluoro-1H-indol-3-yl)-1,2,4-oxadiazol-3-yl]benzyl}amino)propanoic acid;
1-{4-[5-(1-benzyl-1H-indol-3-yl)-1,2,4-oxadiazol-3-yl]benzyl}azetidine-3-carboxylic acid;
3-[5-(1-benzyl-1H-indol-3-yl)-1,2,4-oxadiazol-3-yl]-N-methylpyridin-2-amine;
1-(3,4-dimethylbenzyl)-5-fluoro-3-{3-[4-(1H-imidazol-1-ylmethyl)phenyl]-1,2,4-oxadiazol-5-yl}-1H-indole;

1-(4-{5-[1-(3,4-dimethylbenzyl)-5-fluoro-1H-indol-3-yl]-1,2,4-oxadiazol-3-yl}benzyl)azetidine-3-carboxylic acid;
1-(4-{5-[1-(3,4-dimethylbenzyl)-5-fluoro-2-methyl-1H-indol-3-yl]-1,2,4-oxadiazol-3-yl}benzyl)azetidine-3-carboxylic acid;
3-({4-[5-(1-benzyl-1H-indol-3-yl)-1,2,4-oxadiazol-3-yl]benzyl}amino)propanoic acid;
3-{5-[1-(3,4-dimethylbenzyl)-5-fluoro-1H-indol-3-yl]-1,2,4-oxadiazol-3-yl}-N-methylpyridin-2-amine;
1-(4-{5-[1-(3,4-dimethylbenzyl)-1H-indol-3-yl]-1,2,4-oxadiazol-3-yl}benzyl)azetidine-3-carboxylic acid;
3-[(4-{5-[1-(3,4-dimethylbenzyl)-1H-indol-3-yl]-1,2,4-oxadiazol-3-yl}benzyl)amino]propanoic acid;
1-(4-{5-[1-(3,4-dimethylbenzyl)-5-methyl-1H-indol-3-yl]-1,2,4-oxadiazol-3-yl}benzyl)azetidine-3-carboxylic acid; and
5-({4-[5-(1-benzyl-1H-indol-3-yl)-1,2,4-oxadiazol-3-yl]benzyl}amino)pentanoic acid.

13. A method of treating a disorder associated with sphingosine-1-phosphate (S1P) receptor modulation, which comprises administering to a mammal in need thereof, a pharmaceutical composition comprising a therapeutically effective amount of at least one compound of Formula II

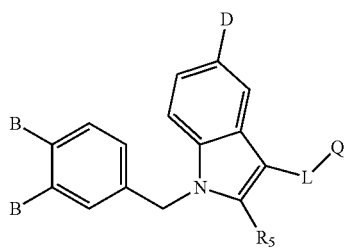

Formula II wherein:
B is the same or is independently $C_{1-4}$ alkyl, methoxy, hydrogen, hydroxyl, halogen, nitrile, trifluoromethyl, amino, carboxylic acid or alkoxy;
D is $C_{1-4}$ alkyl, methoxy, hydrogen, hydroxyl, halogen, nitrile, trifluoromethyl, amino or carboxylic acid;

L is

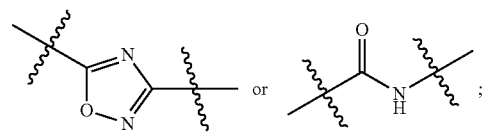 [SMILES: *c1noc(*)n1 ; *NC(*)=O]

Q is one of the following structures:

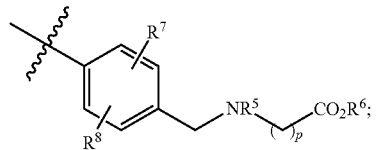

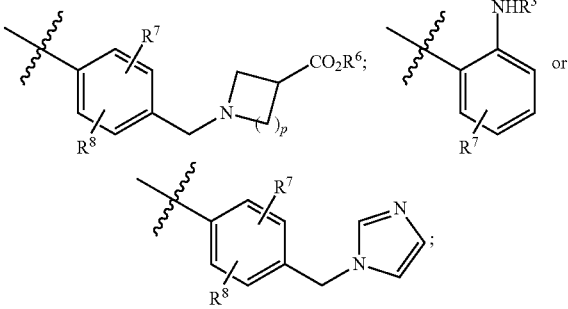

$R^3$ is $C_{1-3}$ alkyl;
$R^5$ is H or Methyl;
$R^6$ is H or Methyl;
p is 1, 2, 3 or 4;
$R_7$ is H, $C_{1-10}$ alkyl, aminoalkyl, halogen, nitrile or trifluoromethyl;
$R_8$ is H, $C_{1-10}$ alkyl, aminoalkyl, halogen, nitrile or trifluoromethyl, wherein a disorder associated with sphingosine-1-phosphate receptor modulation is multiple sclerosis, psoriasis, or organ transplantation.

14. The method of claim 13 wherein the mammal is a human.

* * * * *

UNITED STATES PATENT AND TRADEMARK OFFICE
CERTIFICATE OF CORRECTION

PATENT NO. : 8,530,462 B2
APPLICATION NO. : 13/293821
DATED : September 10, 2013
INVENTOR(S) : Santosh C. Sinha et al.

It is certified that error appears in the above-identified patent and that said Letters Patent is hereby corrected as shown below:

In the Specification

In column 1, line 23, delete "Sphingosine-1 phosphate" and insert -- Sphingosine-1-phosphate --, therefor.

In column 1, lines 53-54, delete "term"modulator"" and insert -- term "modulator" --, therefor.

In column 1, line 65, delete "steroisomeric" and insert -- stereoisomeric --, therefor.

In column 1, line 66, delete "diasteroisomers," and insert -- diastereoisomers, --, therefor.

In column 2, line 35, delete "M" and insert -- m --, therefor.

In column 5, line 65, delete "steroisomeric" and insert -- stereoisomeric --, therefor.

In column 5, line 66, delete "diasteroisomers," and insert -- diastereoisomers, --, therefor.

In column 6, line 19, delete "acid:" and insert -- acid; --, therefor.

In column 6, line 65, delete "steroisomeric" and insert -- stereoisomeric --, therefor.

In column 6, line 66, delete "diasteroisomers," and insert -- diastereoisomers, --, therefor.

In column 7, line 48, delete "steroisomeric" and insert -- stereoisomeric --, therefor.

In column 7, line 49, delete "diasteroisomers," and insert -- diastereoisomers, --, therefor.

In column 8, line 25, delete "steroisomeric" and insert -- stereoisomeric --, therefor.

In column 8, line 26, delete "diasteroisomers," and insert -- diastereoisomers, --, therefor.

In column 9, line 5, delete "steroisomeric" and insert -- stereoisomeric --, therefor.

In column 9, line 6, delete "diasteroisomers," and insert -- diastereoisomers, --, therefor.

In column 10, line 1, delete "steroisomeric" and insert -- stereoisomeric --, therefor.

In column 10, line 2, delete "diasteroisomers," and insert -- diastereoisomers, --, therefor.

In column 10, line 47, delete "steroisomeric" and insert -- stereoisomeric --, therefor.

In column 10, line 48, delete "diasteroisomers," and insert -- diastereoisomers, --, therefor.

In column 11, line 25, delete "steroisomeric" and insert -- stereoisomeric --, therefor.

Signed and Sealed this
Seventeenth Day of December, 2013

Margaret A. Focarino
*Commissioner for Patents of the United States Patent and Trademark Office*

In column 11, line 26, delete "diasteroisomers," and insert -- diastereoisomers, --, therefor.

In column 11, lines 29-39, delete " 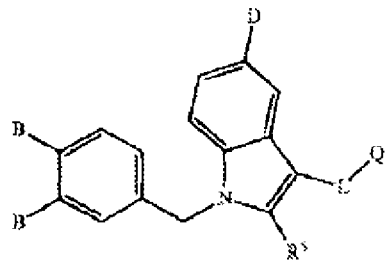 " and insert -- 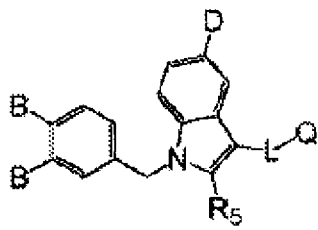 --, therefor.

In column 12, line 5, delete "steroisomeric" and insert -- stereoisomeric --, therefor.

In column 12, line 6, delete "diasteroisomers," and insert -- diastereoisomers, --, therefor.

In column 12, lines 10-20, delete " 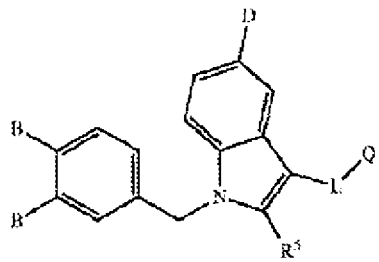 " and insert -- 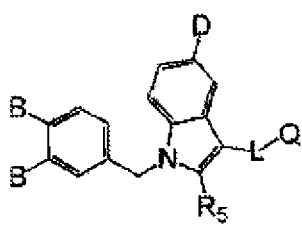 --, therefor.

In column 14, line 47, delete "Chemica" and insert -- Chimica --, therefor.

In column 15, line 24, delete "immnuosuppression:" and insert -- immunosuppression: --, therefor.

In column 15, line 27, delete "antoimmune" and insert -- autoimmune --, therefor.

In column 15, line 28, delete "dermititis," and insert -- dermatitis, --, therefor.

In column 15, line 34, delete "congestional" and insert -- congenital --, therefor.

In column 16, line 17, delete "immnuosuppression:" and insert -- immunosuppression: --, therefor.

In column 16, line 20, delete "antoimmune" and insert -- autoimmune --, therefor.

In column 16, line 21, delete "dermititis," and insert -- dermatitis, --, therefor.

In column 16, line 27, delete "congestional" and insert -- congenital --, therefor.

In column 18, line 22, delete "and or" and insert -- and/or --, therefor.

CERTIFICATE OF CORRECTION (continued)

In column 18, line 54, delete "tertahydrofuran" and insert -- tetrahydrofuran --, therefor.

In column 27, line 16, delete "diasteroisomeric" and insert -- diastereoisomeric --, therefor.

In column 34, line 1, delete "$^1$NMR" and insert -- $^1$H NMR --, therefor.

In column 38, line 57, delete "$^1$HNMR" and insert -- $^1$H NMR --, therefor.

In columns 41-42, line 3, delete "pentanoic" and insert -- propanoic --, therefor.

In column 43, line 26, delete "carboxylic" and insert -- carboxylic acid --, therefor.

In column 47, lines 9-10, delete "dithitothreitol" and insert -- dithiothreitol --, therefor.

In column 47, line 21, delete "pH7.4," and insert -- pH 7.4, --, therefor.

In column 47, line 22, delete "$^{35}$S" and insert -- GTP $\gamma^{35}$S --, therefor.

In the Claims

In column 54, lines 18-25, in claim 13, delete " 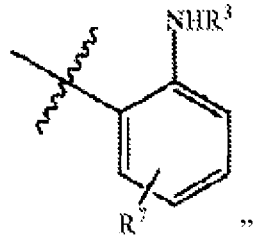 " and insert -- 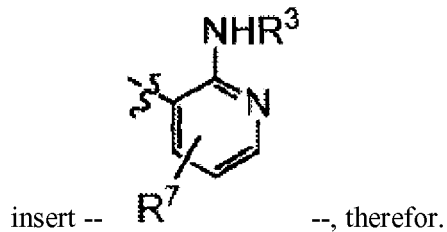 --, therefor.